(12) United States Patent
Campadelli et al.

(10) Patent No.: US 10,421,979 B2
(45) Date of Patent: Sep. 24, 2019

(54) RETARGETED HERPESVIRUS WITH A GLYCOPROTEIN H FUSION

(71) Applicant: ALMA MATER STUDIORUM UNIVERSITA'DI BOLOGNA, Bologna (IT)

(72) Inventors: Maria Gabriella Campadelli, Bologna (IT); Valentina Gatta, Bologna (IT)

(73) Assignee: Alma Mater Studiorum Universita' Di Bologna, Bologna (IT)

( * ) Notice: Subject to any disclaimer, the term of this patent is extended or adjusted under 35 U.S.C. 154(b) by 0 days.

(21) Appl. No.: 15/548,731

(22) PCT Filed: Feb. 11, 2016

(86) PCT No.: PCT/EP2016/052879
§ 371 (c)(1),
(2) Date: Aug. 3, 2017

(87) PCT Pub. No.: WO2016/128497
PCT Pub. Date: Aug. 18, 2016

(65) Prior Publication Data
US 2018/0002723 A1    Jan. 4, 2018

(30) Foreign Application Priority Data
Feb. 11, 2015    (EP) .................................. 15425012

(51) Int. Cl.
| C12N 15/869 | (2006.01) |
| C12N 5/10 | (2006.01) |
| C12N 7/00 | (2006.01) |
| C12N 15/86 | (2006.01) |
| C12N 15/62 | (2006.01) |
| A61K 39/00 | (2006.01) |

(52) U.S. Cl.
CPC ............. *C12N 15/869* (2013.01); *C12N 5/10* (2013.01); *C12N 7/00* (2013.01); *C12N 15/62* (2013.01); *C12N 15/86* (2013.01); *A61K 39/00* (2013.01); *A61K 2039/5254* (2013.01); *A61K 2039/5256* (2013.01); *C12N 2710/16032* (2013.01); *C12N 2710/16632* (2013.01)

(58) Field of Classification Search
None
See application file for complete search history.

(56) References Cited

FOREIGN PATENT DOCUMENTS

| WO | 2009013448 A2 | 1/2009 |
| WO | WO 2009/013448 A2 * | 1/2009 |
| WO | 2009144755 A1 | 12/2009 |

OTHER PUBLICATIONS

International Preliminary Report on Patentability for corresponding PCT Application No. PCT/EP2016/052879, dated Aug. 30, 2017 (9 pages).
Lorentzen, E.U. et al., "Replication-competent herpes simplex virus type 1 mutant expressing an autofluorescent glycoprotein H fusion protein," Intervirology, 2001, vol. 44, No. 4, pp. 232-242.
Cairns, T.M. et al., "Structure-Function Analysis of Herpes Simplex Virus Type 1 gD and gH-gL: Clues from gDgH chimeras," Journal of Virology, vol. 77, No. 12, Jun. 15, 2003.
Atanasiu, D. et al., "Regulation of Herpes Simplex Virus gB-Induced Cell-Cell Fusion by Mutant Forms of gH/gL in the Absense of gD and Cellular Receptors," MBIO, vol. 4, No. 2, Feb. 26, 2011.
Valentina, Gatta et al., "The Engineering of Novel Ligand in gH Confers to HSV an Expanded Tropism Independent of gD Activation by Its Receptors," PLO

RETARGETED HERPESVIRUS WITH A GLYCOPROTEIN H FUSION

This application is the U.S. national phase application, pursuant to 35 U.S.C. § 371, of PCT International Application Ser. No.: PCT/EP2016/058279, filed Feb. 11, 2016, designating the United States and published in English, which claims the benefit of European Patent Application No. 15425012.0, filed Feb. 11, 2015, entitled "Retargeted Herpesvirus with a Glycoprotein H Fusion," the entire contents of which are incorporated herein by reference.

FIELD OF THE INVENTION

The present invention relates to the field of disease therapy. More specifically, it relates to a retargeted herpesvirus having a heterologous polypeptide fused to glycoprotein H, wherein the polypeptide targets specific cells, in particular diseased cells. It also relates to a nucleic acid comprising the genome of the herpesvirus of the invention, a vector comprising this nucleic acid and a cell comprising the nucleic acid or the vector. It further relates to killing cells using the herpesvirus of the invention and to methods for growing it in vitro.
The work leading to this invention has received funding from the European Research Council under the European Union's Seventh Framework Programme (FP7/2007-2013)/ERC grant agreement no 340060.

BACKGROUND OF THE INVENTION

The burden of diseases and pathologies that cannot be treated, and less so cured, remains elevated, notwithstanding the high number of discoveries that in the past decades were translated into therapies or cures, and resulted in improvements to health and quality of life of humans. Eminent among these are numerous forms of cancers, in particular metastatic forms of cancers, that are treated with chemo-radio-therapy or biological medicaments, or combinations thereof, with very limited success.

In the past two decades there have been numerous efforts to employ herpes simplex viruses (HSVs) as oncolytic agents (o-HSVs) to treat cancers and metastases. Examples are genetically engineered HSVs, which carry deletions of some of the viral genes in order to attenuate the viruses, and confer some degree of cancer specificity. These viruses, exemplified by the virus named HSV1716, carry the deletion of one or both copies of the $\gamma_1 34.5$ gene, whose product contrasts the host defence exerted by activation of PKR (protein kinase R). The HSVs carrying the deletion of the $\gamma_1 34.5$ gene gain their partial cancer-specificity by the fact that non-cancer cells mount an innate response against them such that viral replication is hindered; by contrast, some of the cancer cells exhibit defects in the innate response, and thus allow the $\Delta \gamma_1 34.5$ HSV to replicate, and consequently to kill the cancer cells. A weakness of these o-HSVs is that cancer cells are heterogeneous, and the $\Delta \gamma_1 34.5$ HSV can only kill the fraction of cancer cells defective in PKR response. For safety reasons and to achieve an improved cancer-specificity, in some instances the $\Delta \gamma_1 34.5$ HSVs have been engineered to carry further deletions, exemplified by deletion of the UL 39 gene encoding the large subunit of ribonucleotide reductase, deletion of ICP 47, etc. These additional deletions result in a further attenuation of the o-HSVs.

To overcome the limited oncolytic effect consequent to attenuation, the o-HSVs carrying the deletion of $\gamma_1 34.5$ gene, or combination of deletions, have been further modified to encode for a chemokine or cytokine. The two pertinent examples are T-VEC and M032. The o-HSV initially named Onco-Vex, and later renamed T-Vec, encodes GM-CSF, which favours the recruitment and maturation of monocytes and dendritic cells, and thus augments the response of the treated patient to its own tumor. The effect is an enhancement of the clearance of tumors by the immune system of the treated patient. In a phase III clinical trial, it improved the outcome of patients carrying metastatic melanoma. The second example is M032, a $\Delta \gamma_1 34.5$ HSV engineered to encode the sequence of IL12. This virus is predicted to favour a Th1 response. Recruitment of patients affected by glioblastoma for treatment with M032 in a phase1 trial is open. The major limits of the attenuated viruses are twofold, (i) their overall decreased replication, which represents an obstacle both in vivo, and with respect to the production of virus stocks large enough to yield efficacious inocula; and (ii) and their limited cancer-specificity due to their ability to enter and be sequestered by normal cells. These two limits are expected to be detrimental for the clinical efficacy of the treatment.

One approach to overcome these limits has been the genetic engineering of o-HSVs which exhibit a highly specific tropism for the cancer cells, and are otherwise not attenuated. This approach has been defined as retargeting of HSV tropism to cancers-specific receptors. HSV enters cells by fusion of its envelope with cell membranes; these are either the plasma membrane or the membrane bounding the endocytic vesicles. In the latter case, the attachment of the virus to the cell surface is followed by uptake of the virus by the cell into endocytic vesicles, and subsequently by fusion of the virion envelope with the membrane of the endocytic vesicle. The virion envelope is the most external structure of the HSV particle; it consists of a membrane which carries a number of virus-encoded glycoproteins that are activated in a cascade fashion to promote the fusion of the HSV envelope with cell membranes. These glycoproteins are gC and gB, which mediate a first attachment of the HSV particle to cell surface heparan sulphate. Thereafter, gD interacts with at least two independent, alternative cell surface receptors, named Nectin 1 and HVEM or HVEA. The binding site of Nectin 1 or of HVEM on gD differ. The interaction of gD with one of the two alternative receptors induces conformational changes in gD, which are thought to activate the downstream glycoproteins gH/gL (which form a heterodimer) and gB, in a cascade fashion. gB executes the fusion of the virion envelope with the cell membrane.

The retargeting of HSV to cancer-specific receptors entails the genetic modifications of gD, such that it harbours heterologous sequences which encode for a specific ligand. Upon infection with the recombinant virus which encodes the chimeric gD-ligand glycoprotein, progeny virions are formed which carry in their envelope the chimeric gD-ligand glycoprotein, in place of wt-gD. The ligand interacts with a molecule specifically expressed on the selected cancer cell, or on a group of cancers, and enables entry of the recombinant o-HSV in the selected cancer cell. Examples of ligands that have been successfully used for retargeting of HSV are IL13α, uPaR, a single chain antibody to HER2 and a single chain antibody to EGFR.

Previous studies have disclosed the construction of two recombinants named R-LM113 and R-LM249, both retargeted to the HER2 cancer receptor. To achieve a high degree of cancer specificity, the interaction of gD with its natural receptors Nectin 1 and HVEM was abolished through deletions of specific portions of the gD molecule. R-LM113 carries the deletion of the mature gD sequence corresponding to AA 6-38. R-LM249 carries the deletion of the core region of mature gD, corresponding to AA 61-218. In both viruses, the deleted sequences were replaced with the sequence encoding a single chain antibody (sc-Fv) derived from trastuzumab, a monoclonal antibody to HER2.

The retargeting through modification of glycoproteins other than gD has been attempted with gC. The inserted ligands were EPO and IL13. The virus carrying the gC-EPO chimera attached to cells expressing the EPO receptors; however this attachment did not lead to infectious entry; rather, the virus was degraded, possibly because it was taken in and ended up in lysosomes; all in all this strategy did not result in a viable retargeted virus. The gC-IL13 chimera was present in a virus that carried a second copy of IL13 in the gD gene. The virus was retargeted. Inasmuch as all viable retargeted HSV carry the retargeting ligand in gD, it cannot be inferred from those studies whether the gC-IL13 contributed or not to the retargeting to the IL13 alpha2 receptor.

The retargeting through genetic modifications of HSV gB has, to the knowledge of the inventors, never been described.

The retargeting through genetic modifications of gH/gL has, to the knowledge of the inventors, never been described, or even been attempted.

Pertinent to the present invention are the previous findings of Cairns et al. (Journal of Virology, June 2003, Vol. 77, No. 12, p. 6731-6742), summarized in the following. In an attempt to understand which role gL plays in the heterodimer gH/gL, the deletion of the gL gene was introduced in the herpesvirus named pseudorabiesvirus (PrV), a swine herpesvirus with high homology to the human HSV. The ΔgL PrV was not viable, since it could not infect, hence could not replicate. Serial blind passages of this virus gave rise to a spontaneous mutant, named PrV-ΔgLPass, which carried a chimeric glycoprotein made of the gD sequence fused to the N-terminus of gH. An essentially similar chimera was subsequently engineered also with the corresponding HSV genes. It carries the sequence encoding the signal peptide of gD and the ectodomain of mature gD (aa 1-308) fused at the N-terminus of the mature gH. Examples where gH was partially deleted did not give rise to any functional molecule. The property of the gD-gH glycoprotein, in which the entire ectodomain of gD was fused to the N-terminus of gH (named chimera 22 in Cairns et al., supra) is pertinent here. Of note, in wt virus, the activation exerted by the receptor-bound gD on gH/gL necessarily occurs through intermolecular signaling. The inventors refer to it as trans-signaling, as opposed to a signaling that occurs intramolecularly, herein referred to as cis-signaling. It is a surprising discovery of the present inventors that the activation of gH can occur in cis. This is the case for constructs R-VG803 and R-VG809, in which the sc-Fv activates the gH moiety in the chimera itself. The chimera 22 by Cairns et al., supra, was employed in complementation assays. Specifically, the chimera 22 rescued infection of a $gD^{-/-}$ $gH^{+/+}$ virus, or of a $gH^{-/-}$ $gD^{+}$ virus. It was not tested for complementation of a double deletion $gD^{-/-}$ $gH^{-/-}$ virus. There are two key differences between the previous report and the present finding. First, in the complementation assays (Cairns et al., supra), the wt-gD in the $gH^{-/-}$ $gD^{+}$ virus may have activated in trans the gH moiety which is part of the gD-gH chimera. Conversely, the gD moiety, which is part of the chimera, may have activated in trans the wt-gH present in the $gD^{-/-}$ $gH^{+}$ virions. In either case, the activation can only have taken place in-trans, as concluded by Cairns et al., supra. Evidence for cis-activation of the gD-gH chimera was not provided and would not have been considered possible by the skilled person. Secondly, irrespective of the activation mechanism, in the complementing system the gH activation was mediated by gD, which has a binding site for gH, and not by a heterologous ligand. These results did not establish or suggest that heterologous sequences (sequences other than viral sequences), herein named ligand, could be introduced at the N-terminus of gH and even less so whether a heterologous ligand introduced at the N-terminus of gH could serve the function of retargeting the HSV tropism to a cellular receptor capable to bind the engineered ligand.

The present inventors have shown that this can indeed be done and that gH can be modified to retarget herpesvirus.

SUMMARY OF THE INVENTION

In a first aspect, the present invention relates to a recombinant infectious herpesvirus comprising a heterologous polypeptide ligand fused to the N-terminus of mature glycoprotein H (gH) or of a truncated gH, or inserted into gH.

In a second aspect, the present invention relates to the recombinant infectious herpesvirus of the first aspect for use in the treatment of a disease.

In a third aspect, the present invention relates to a nucleic acid comprising the genome of the recombinant infectious herpesvirus of the first aspect or at least its heterologous polypeptide ligand fused to the N-terminus of mature gH or of a truncated gH, or inserted into gH.

In a fourth aspect, the present invention relates to a vector comprising the nucleic acid of the third aspect.

In a fifth aspect, the present invention relates to a cell comprising the recombinant infectious herpesvirus of the first aspect, the nucleic acid of the third aspect or the vector of the fourth aspect.

In a sixth aspect, the present invention relates to the recombinant infectious herpesvirus of the first aspect for medical use.

In a seventh aspect, the present invention relates to a method of killing a cell using the recombinant infectious herpesvirus of the first aspect.

In an eighth aspect, the present invention relates to an in vitro method for growing the recombinant infectious herpesvirus of the first aspect in cells.

In a preferred embodiment of the invention, the recombinant infectious herpesvirus has a glycoprotein D (gD) with an amino acid deletion resulting in the de-targeting of the herpesvirus from molecules or parts thereof accessible on the surface of a cell which are targeted by unmodified gD. Also or alternatively, the gD comprises a heterologous polypeptide ligand fused to the N-terminus of mature gD or of a truncated gD, or inserted into gD.

LEGENDS TO THE FIGURES

FIG. 1: Genome arrangements of recombinants R-VG803, R-VG811, R-VG809, R-VG805 and R-VG807. The HSV-1 genome is represented as a line bracketed by Internal repeats (IR). The Lox-P-bracketed BAC sequence is inserted in the intergenic region UL3-UL4. The m-Cherry red fluorescent marker is inserted in the intergenic region UL37 and UL38. R-VG803 carries the insertion of scFv-HER2, bracketed by Ser-Gly linkers, between AA 23-24 of gH. R-VG811 carries the insertion of scFv-HER2, bracketed by Ser-Gly linkers, between AA 23-48 of gH. R-VG809 is otherwise identical to R-VG803. In addition it carries the deletion of AA 6-38 from mature gD. R-VG805 is otherwise identical to R-VG809; in addition it carries the insertion of scFv-EGFR in place of AA 6-38 from mature gD. R-VG807 is otherwise identical to R-VG809; in addition it carries the insertion of scFv-HER2 in place of AA 6-38 from mature gD.

FIG. 2: R-VG803 and R-VG 809 express the chimeric scFv-gH glycoprotein. Lysates of Vero cells infected with R-VG803, R-VG809 or R-LM5 were subjected to PAGE. gH was detected by immunoblot. Numbers on the left represent the migration position of the 130K and 95K MW markers.

FIG. 3: R-VG803 infects cells that express HER2 as the sole receptor (J-HER2 cells) as well as cells positive for the natural gD receptors, and progeny virus spreads from cell to cell in J-HER2 cells. J cells express no receptor for wt-HSV. J-HER2, J-Nectin1, J-HVEM only express the indicated receptor. (A) The indicated cells were infected with R-VG803 (1 PFU/cell as titrated in J-HER2 cells), and monitored for red fluorescence microscopy. (B) J-HER2 cells were infected with R-VG803 (0.01 PFU/cell), maintained in medium containing MAb 52S and monitored daily for red fluorescence. Increase in plaque size denotes cell-to-cell spread.

FIG. 4: Characterization of R-VG803 entry pathways in J-HER2 (A-B) and of R-VG803 and R-VG809 entry pathways in SK-OV-3 (C) cells. (A, B) Trastuzumab inhibits R-VG803 infection of J-HER2 cells. J-HER2 cells were infected with R-VG803 in the presence of trastuzumab (trastuz) (28 µg/ml) or control IgGs. Infection was monitored by fluorescence microscopy (A), or flow cytometry (B). (C) Effects of trastuzumab and HD1 MAbs on infection of SK-OV-3 cells with R-VG803, or R-VG809. R-VG803 was preincubated with the HD1 (final concentration 1 µg/ml) and then allowed to infect SK-OV-3 cells, in triplicates. When indicated, cells were pretreated with trastuzumab (final concentration 28 µg/ml). Extent of infection was quantified 24 h later by means of flow cytometry (BD Accuri C6), and expressed as percentage relative to cells infected with untreated virus. Each value represents the average of triplicates.

FIG. 5: R-VG809 infects cells which express HER2 as the sole receptor (J-HER2, CHO-HER2), as well as SK-OV-3 cells, and fails to infect J-HVEM, J-Nectin, and human and animal cells negative for HER2 expression and positive for the natural gD receptors. Cells were infected at 3 PFU/cell and monitored for infection 24 h later.

FIG. 6: R-VG805 infects J-HER2, J-EGFR, CHO-EGFR, U251-EGFR-vIII cells, and fails to infect J-Nectin1 and J-HVEM cells, as well as the receptor-negative wt-CHO-KI cells.

FIG. 7: Infection with R-VG811 of J-HER2, SK-OV-3, as well as J-Nectin1 and J-HVEM cells (A), and determination of the extent of virus infection (B-D). (A) R-VG811 infects J-HER2, SK-OV-3, as well as J-Nectin1 and J-HVEM cells. (B) Comparison of the amount of infected cells obtained upon transfection of R-VG811, or R-VG803 DNA-BAC in J-HER2 or SK-OV-3 cells. (C-D) Quantification of infection in cells transfected with DNA_BAC by means of m-cherry detection.

FIG. 8: Replication curve of R-VG803 and R-VG809, in comparison to R-LM113, R-LM249, and R-LM5 in J-HER2, or SK-OV-3 cells. (A) Growth curves of R-VG803, and of R-LM113 in J-HER2, (B) growth curves of R-VG803, R-VG809 and R-LM5 in J-HER2. R-VG803, R-VG809, R-LM113, R-LM249 and R-LM5 in SK-OV-3 (C) cells. Cells were infected at 0.1 PFU/cell (A, C) or 0.01 PFU/cell (B) of virus titrated in the same cell line, harvested at indicated times. Progeny virus was titrated in J-HER2 (A, B) or SK-OV-3 (C) cells. Results are the average of at least two independent experiments.

FIG. 9: Killing ability of R-VG803 and R-VG809 for SK-OV-3 cells, in comparison to killing ability of R-LM113, R-LM249, and R-LM5. Results are shown as viability of SK-OV-3 cells, infected with the indicated viruses at 2 PFU/cell, as determined by AlamarBlue, in triplicate monolayers. The figure represents the average of triplicates.

DETAILED DESCRIPTION OF THE INVENTION

Figure 1:
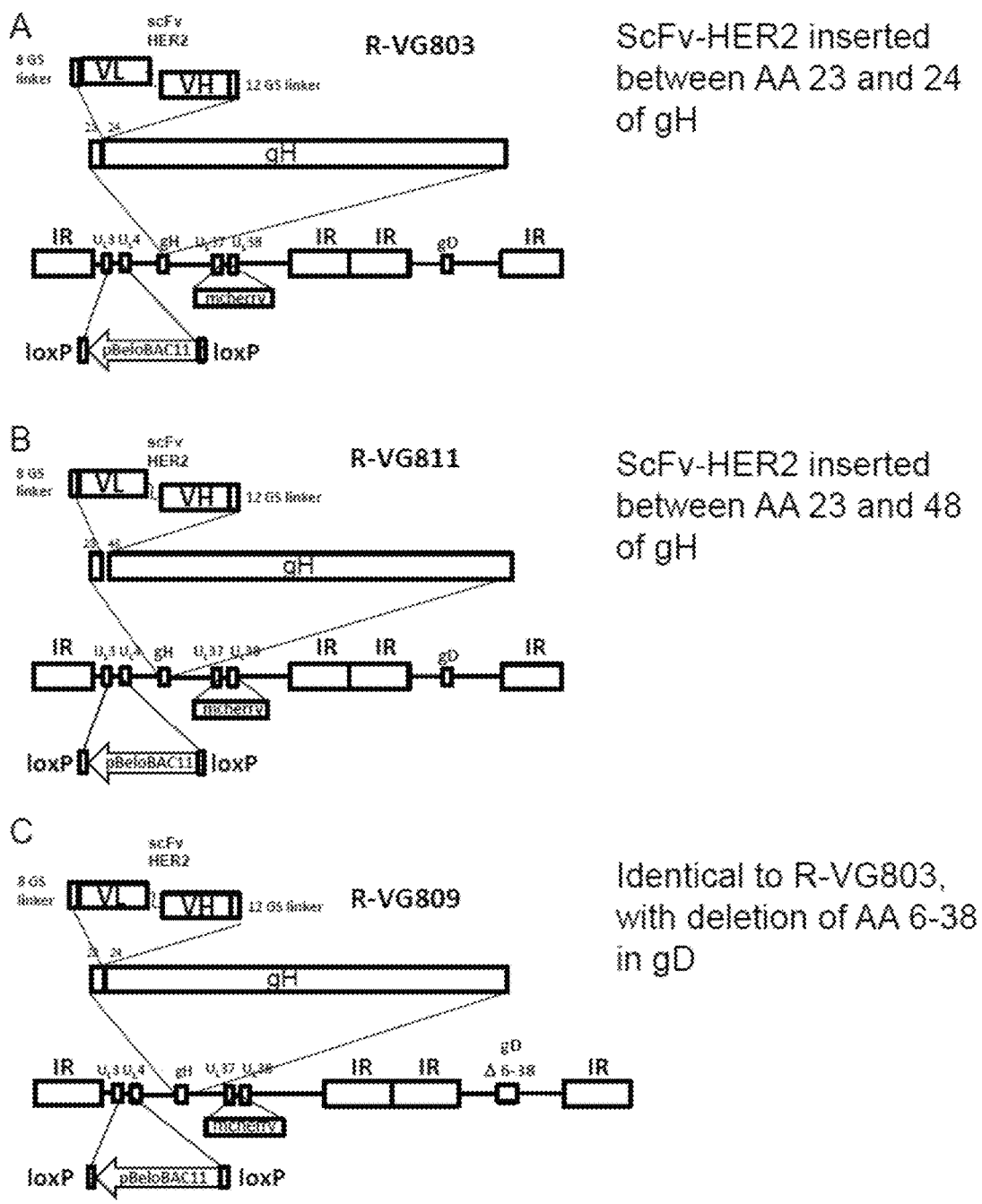
Figure 1:
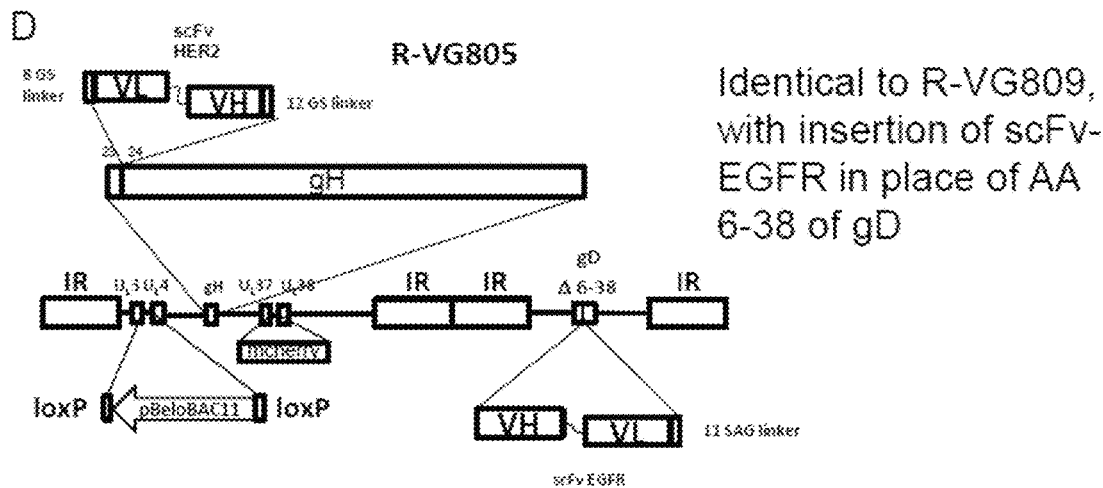
Figure 1:
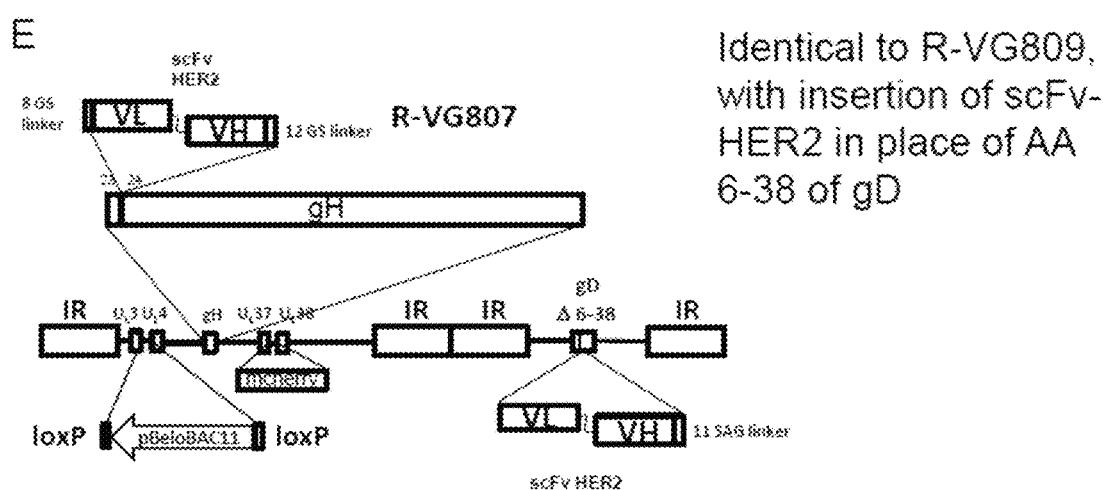
Figure 2:
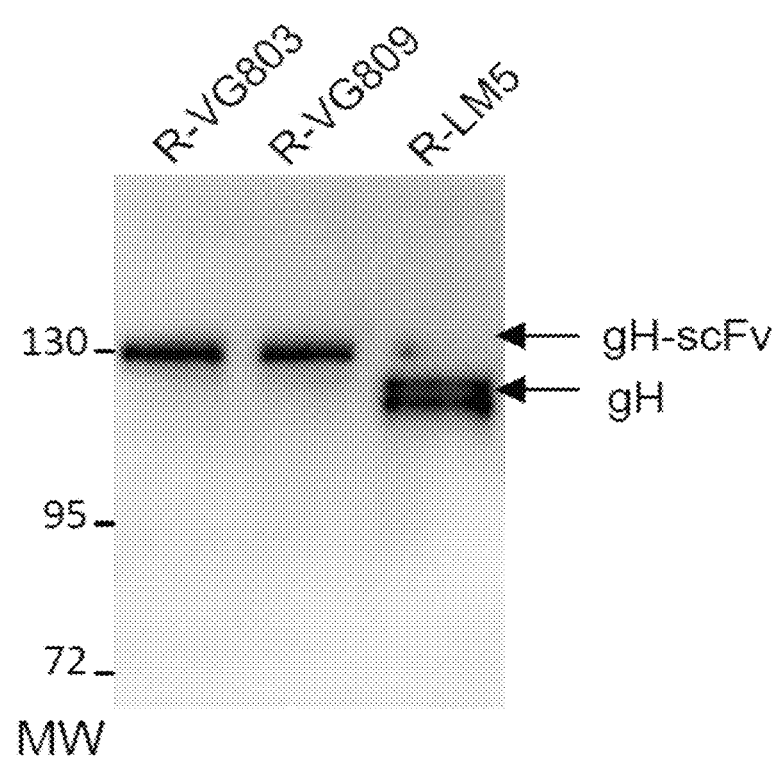

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In a first aspect, the present invention relates to a recombinant infectious herpesvirus comprising a heterologous polypeptide ligand fused to the N-terminus of mature glycoprotein H (gH) or of a truncated gH, or inserted into gH (also referred to herein as modified gH).

The term "recombinant" herpesvirus as used herein refers to a herpesvirus that has been genetically engineered to express a heterologous protein. Methods of creating recombinant herpesviruses are well known in the art, see for example Sandri-Goldin et al., Alpha Herpesviruses: Molecular and Cellular Biology, Caister Academic Press, 2006.

The term "infectious" herpesvirus as used herein refers to a herpesvirus which is capable of entering a target cell and of producing proteins encoded by the viral genome, including heterologous proteins comprised therein. In a preferred meaning, the herpesvirus is also capable of producing progeny virus in the entered target cell.

The term "herpesvirus" as used herein refers to a member of the herpesviridae family of double-stranded DNA viruses, which cause latent or lytic infections. Herpesviruses all share a common structure: all herpesviruses are composed of relatively large double-stranded, linear DNA genomes encoding 100-200 genes encased within an icosahedral protein cage called the capsid which is itself wrapped in a protein layer called the tegument containing both viral proteins and viral mRNAs and a lipid bilayer membrane called the envelope. This whole particle is also known as a virion.

The term "heterologous" polypeptide as used herein with respect to herpesvirus refers to a polypeptide that is not native to the herpesvirus. At least it is not native to the particular herpesvirus strain used, but in a preferred meaning it is also not native to any other herpesvirus. The term also excludes proteins derived from a herpesvirus, which are genetically altered, i.e. such genetically altered herpesvirus proteins are not heterologous polypeptides within the defined meaning of the term. In a particular embodiment, the heterologous polypeptide ligand is not herpesvirus glycoprotein D (gD) or a fragment thereof that specifically binds a cellular ligand of gD.

The term "fused" or "fusion" as used herein refers to the linking of two different polypeptides by peptide bonds, either directly or indirectly via one or more peptide linkers. In a preferred embodiment relating to gH, the heterologous polypeptide ligand is fused to the N-terminus of mature gH or of a truncated mature gH. In a preferred embodiment relating to gD, the heterologous polypeptide ligand is fused to the N-terminus of mature gD or of a truncated mature gD.

A peptide linker has a length between 1 and 30 amino acids, preferably 5 to 15 amino acids, more preferably 8-12 amino acids, and may consist of any amino acids. Preferably, it comprises the amino acid(s) Gly and/or Ser, more preferably it comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids selected from the group consisting of Gly and Ser. Most preferably, it consists of the amino acids Gly and/or Ser. Linkers based on Gly and Ser are preferable because they provide flexibility, good solubility and resistance to proteolysis.

The term "mature" glycoprotein as used herein refers to a glycoprotein lacking the N-terminal signal peptide. With respect to gH, it preferably refers to gH lacking amino acids 1-18 of the gH according to SEQ ID NO: 1 or a corresponding region of a homologous gH. With respect to gD, it preferably refers to gD lacking amino acids 1-25 of the gD according to SEQ ID NO: 4 or a corresponding region of a homologous gD.

The term "truncated" glycoprotein as used herein refers to a herpesvirus glycoprotein, preferably a mature herpesvirus glycoprotein lacking an N-terminal portion. In a particular embodiment, gH is truncated up to (i.e. the truncation including) any of amino acids 18 to 88 (i.e. 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87 or 88) in particular amino acid 23, 24, 48, 50, or 88 of the gH according to SEQ ID NO: 1 (a truncation up to amino acid 18 results in the mature gH). In another particular embodiment, gD is truncated up to (i.e. the truncation including) any of amino acids 25 to 64 (i.e. 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63 or 64), in particular amino acid 64 of the gD according to SEQ ID NO: 4 (a truncation up to amino acid 25 results in the mature gD).

The term "glycoprotein H" or "gH" as used herein refers to a 110 kDa virion envelope glycoprotein that plays a role in herpesvirus infectivity. In particular, in forms a heterodimer with herpesvirus glycoprotein L. Herein it is represented by gH of HSV-1 according to SEQ ID NO: 1 (gH precursor or full-length gH, which includes the signal sequence; the mature gH lacks this signal sequence, i.e. residues 1-18 of SEQ ID NO: 1). However, gH homologues are found in all members of the herpesvirus family and, as such, homologous sequences may vary (see also below for preferred homologues). Thus, HSV-1 gH homologues are also encompassed by the invention. In a preferred embodiment, such HSV-1 gH homologues have an amino acid sequence that is at least 70%, 80%, 85%, 90%, 95%, 96%, 97%, 98% or 99% identical to the sequence according to SEQ ID NO: 1 and they retain, preferably as wildtype (i.e. unmodified), the capability of forming a heterodimer with herpesvirus glycoprotein L. Among at least human and monkey herpesviruses, gH is conserved. Crystal structures of the extracellular portion of three gH proteins are known: one from the alphaherpesvirus HSV-2 gH (Chowdary et al., Nat Struct Mol Biol 2010 17:882-888), one from the swine PrV (Backovic et al., PNAS 2012 107(52) 22635-22640), also an alphaherpesvirus, and one from Epstein-Barr virus (Matsuura et al., PNAS, 2010 107(52) 22641-22646), a gamma herpesvirus. They are substantially similar, for example, an organization in structurally similar domains is present in all crystal structures.

The term "gD" or "glycoprotein D" refers to a component of the virion envelope of herpesvirus which plays an essential role in HSV entry into cells. gD binds to a cellular molecules, namely HVEM and Nectin-1 following the initial interaction of herpesvirus glycoproteins gC and gB with heparan sulfate proteoglycans. Herein it is represented by gD of HSV-1 according to SEQ ID NO: 4 (gD precursor or full-length gD), which includes the signal sequence; the mature gD lacks this signal sequence, i.e. residues 1-25 of SEQ ID NO: 4). However, homologous gD (see also below for preferred homologues) are found in other members of the herpesvirus family and, as such, homologous sequences may vary. Thus, HSV-1 gD homologues are also encompassed by the invention. In a preferred embodiment, such HSV-1 gD homologues have an amino acid sequence that is at least 70%, 80%, 85%, 90%, 95%, 96%, 97%, 98% or 99% identical to the sequence according to SEQ ID NO: 4 and they retain, as wildtype (i.e. unmodified), the capability of binding to HVEM and Nectin-1 or, more general, to cellular receptors enabling the gD homolog to promote, in a cascade fashion, fusion of the viral envelope with cell membranes.

In a preferred embodiment, the herpesvirus is selected from the group consisting of Herpes Simplex Virus 1 (HSV-1), Herpes Simplex Virus 2 (HSV-2), Varicella Zoster Virus (human herpesvirus 3 (HHV-3)), swine alphaherpesvirus Pseudorabievirus (PRV), Chimpanzee alpha1 herpesvirus (ChHV), Papiine herpesvirus 2 (HVP2), Cercopithecine herpesvirus 2 (CeHV2), Macacine herpesvirus 1 (MHV1), Saimiriine herpesvirus 1 (HVS1), callitrichine herpesvirus 3 (CalHV3), Saimiriine herpesvirus 2 (HVS2), Bovine herpesvirus 1 (BoHV-1), Bovine Herpesvirus 5 (BoHV-5), Equine herpesvirus 1 (EHV-1), Equine herpesvirus 2 (EHV-2), Equine herpesvirus 5 (EHV-5), Canine herpesvirus 1 (CHV), Feline herpesvirus 1 (FHV-1), Duck enteritis virus (DEV), Fruit bat alphaherpesvirus 1 (FBAHV1), Bovine herpesvirus 2 (BoHV-2), Leporid herpesvirus 4 (LHV-4), Equine herpesvirus 3 (EHV-3), Equine herpesvirus 4 (EHV-4), Equine herpesvirus 8 (EHV-8), Equid herpesvirus 9 (EHV-9), Cercopithecine herpesvirus 9 (CeHV-9), Suid herpesvirus 1 (SuHV-1), Marek's disease virus (MDV), Marek's disease virus serotype 2 (MDV2), Falconid herpesvirus type 1 (FaHV-1), Gallid herpesvirus 3 (GaHV-3), Gallid herpesvirus 2 (GaHV-2), Lung-eye-trachea disease-associated herpesvirus (LETV), Gallid herpesvirus 1 (GaHV-1), Psittacid herpesvirus 1 (PsHV-1), Human herpesvirus 8 (HHV-8), Human herpesvirus 4 (HHV-4), Chelonid herpesvirus 5 (ChHV5), Ateline herpesvirus 3 (AtHV3) or Meleagrid herpesvirus 1 (MeHV-1). These viruses all have at least a gH with clear homology to the gH of HSV-1/-2. In a more preferred embodiment, the herpesvirus is HSV-1 or HSV-2.

The term "inserted" or "insertion" as used herein refers to the incorporation of one polypeptide into another polypeptide, wherein the incorporated polypeptide is linked to the host polypeptide by peptide bonds, either directly or indirectly via one or more peptide linkers, more specifically via an N-terminal and/or C-terminal peptide linker with respect to the insert. Although the fusion of a peptide ligand to mature gH/gD can also be seen as an insertion into the gH/gD precursor according to SEQ ID NOs 1/4, respectively, such an insertion is herein termed as an N-terminal fusion since the virion carries the mature glycoprotein. Thus, the term "insertion" preferably refers to an insertion into a mature glycoprotein, in particular gH and gD.

In a preferred embodiment, the heterologous polypeptide ligand is inserted within the N-terminal region of gH starting at any one of amino acids 19 to 23 (preferably 19) and ending at any one of amino acids 48 to 88 (preferably 88), preferably starting at amino acid 19 and ending at amino acid 88, starting at amino acid 61 and ending at amino acid 65, starting at amino acid 69 and ending at amino acid 72, or starting at amino acid 74 and ending at amino acid 80; or starting at amino acid 116 and ending at amino acid 136 of the gH according to SEQ ID NO: 1 or a corresponding region of a homologous gH. The ranges 61-65, 69-72 and 74-80 are thought to be particularly useful since they represent exposed-loop regions of the gH H1A domain and therefore represent insertion points that retain the structural integrity of the gH H1A domain. In a more preferred embodiment, it is inserted within the N-terminal region of gH starting at amino acid 19 and ending at amino acid 50 of the gH according to SEQ ID NO: 1 or a corresponding region of a homologous gH. In an even more preferred embodiment, it is inserted within the N-terminal region of gH starting at amino acid 19 and ending at amino acid 48 of the gH according to SEQ ID NO: 1 or a corresponding region of a homologous gH. In another more preferred embodiment, it is inserted within the N-terminal region of gH starting at amino acid 23 and ending at amino acid 48 of the gH according to SEQ ID NO: 1 or a corresponding region of a homologous gH. In all these embodiments, the amino acids defining start and end of a region are included in the region, i.e. the insertion may by either N-terminal or C-terminal of the start or end amino acid. In the particular case of an insertion N-terminal of residue 19 of SEQ ID NO: 1, the insertion can also be seen as a fusion to the N-terminus of mature gH. Thus, to distinguish the terms "insertion" and "fusion" clearly, this particular case is preferably excluded from the possible insertions and falls under a fusion to the N-terminus of mature gH as described.

Furthermore, in all these embodiments, said region may be replaced by the insertion. The particular case of the insertion replacing a region comprising residue 19 of SEQ ID NO: 1, the insertion can also be seen as a fusion to the N-terminus of a truncated mature gH. Thus, to distinguish the terms "insertion" and "fusion" clearly, this particular case is preferably excluded from the possible insertions and falls under a fusion to the N-terminus of a truncated mature gH as described.

In the most preferred embodiment, the ligand is inserted between amino acid 23 and amino acid 24 of the gH according to SEQ ID NO: 1 or a corresponding region (in this case corresponding to said amino acids 23 and 24) of a homologous gH.

In a particular embodiment, one or more gH amino acids of the N-terminal region as specified above are deleted. In a related embodiment, gH is truncated as specified above.

The term "corresponding region of a homologous gH" refers to a region of a gH which aligns with a given region of HSV-1 gH (preferably the region of the insertion as defined above) according to SEQ ID NO: 1 when using the Smith-Waterman algorithm and the following alignment parameters: MATRIX: BLOSUM62, GAP OPEN: 10, GAP EXTEND:

0.5. In case only a part or parts of the given region of HSV-1 gH aligns with the sequence of a homologous gH using above algorithm and parameters, the term "corresponding region of a homologous gH" refers to the region which aligns with the part(s) of the given region of HSV-1 gH. In other words, in this case the region in the homologous gH, in which the ligand is inserted or which is replaced by the ligand, comprises only the amino acids which align with the part(s) of the given region of HSV-1 gH. Also, in the same case, the term "corresponding region of a homologous gH" may refer to a region which is flanked by corresponding flanking sequences, wherein corresponding flanking sequences are sequences of the homologous gH which align, using above algorithm and parameters, with sequences flanking the above given region (preferably the region of the insertion as defined above) of HSV-1 gH. These flanking sequences of HSV-1 gH are at least 5, 6, 7, 8, 9, 10, 15, 20, 30, 40 or 50 amino acids long (the flanking sequence at the N-terminus of gH, i.e. N-terminal any of amino acid residue 19 to 23 according to SEQ ID NO: 1 may be shorter, i.e. as specified but up to 18, 19, 20, 21, or 22 amino acid residues long) and align with the sequence of a homologous gH using above algorithm and parameters.

The homologous gH is preferably gH of Herpes Simplex Virus 2 (HSV-2), Varicella Zoster Virus (human herpesvirus 3 HHV-3), swine alphaherpesvirus Pseudorabievirus (PRV), Chimpanzee alpha1 herpesvirus (ChHV), Papiine herpesvirus 2 (HVP2), Cercopithecine herpesvirus 2 (CeHV2), Macacine herpesvirus 1 (MHV1), Fruit bat alphaherpesvirus 1 (FBAHV1), Saimiriine herpesvirus 1 (HVS1), callitrichine herpesvirus 3 (CalHV3), Saimiriine herpesvirus 2 (HVS2), Bovine herpesvirus 1 (BoHV-1), Bovine Herpesvirus 5 (BoHV-5), Equine herpesvirus 1 (EHV-1), Equine herpesvirus 2 (EHV-2), Equine herpesvirus 5 (EHV-5), Canine herpesvirus 1 (CHV), Feline herpesvirus 1 (FHV-1), Cercopithecine herpesvirus 9 (CeHV-9), Duck enteritis virus (DEV, AnHV-1), Bovine herpesvirus 2 (BoHV-2), Leporid herpesvirus 4 (LHV-4), Equine herpesvirus 3 (EHV-3), Equine herpesvirus 4 (EHV-4), Equine herpesvirus 8 (EHV-8), Equid herpesvirus 9 (EHV-9, Marek's disease virus (MDV), Marek's disease virus serotype 2 (MDV2), Gallid herpesvirus 3 (GaHV-3), Gallid herpesvirus 2 (GaHV-2), Lung-eye-trachea disease-associated herpesvirus (LETV), Gallid herpesvirus 1 (GaHV-1), Psittacid herpesvirus 1 (PsHV-1), Human herpesvirus 8 (HHV-8), Human herpesvirus 4 (HHV-4), Falconid herpesvirus type 1 (FaHV-1), Chelonid herpesvirus 5 (ChHV5), Ateline herpesvirus 3 (AtHV3) or Meleagrid herpesvirus 1 (MeHV-1). These herpesviruses and HSV-1 have gH sequences that are highly conserved with respect to that of HSV-1. More preferably the homologous gH is gH of Herpes Simplex Virus 2 (HSV-2), Chimpanzee alpha1 herpesvirus (ChHV), Papiine herpesvirus 2 (HVP2), Cercopithecine herpesvirus 2 (CeHV2), Macacine herpesvirus 1 (MHV1), Fruit bat alphaherpesvirus 1 (FBAHV1), Bovine herpesvirus 2 (BoHV-2) or Leporid herpesvirus 4 (LHV-4). Most preferably the homologous gH is gH of Herpes Simplex Virus 2 (HSV-2).

In another embodiment, the heterologous polypeptide ligand is inserted N-terminally of the H1A domain of gH. N-terminally inserted in this respect does not mean adjacent to the H1A domain on the N-terminal side, but anywhere on the N-terminal side of the H1A domain. The H1A domain of gH is a subdomain of the H1 domain of gH. The H1 domain extends from amino acid 49 to 327 of the gH protein according to SEQ ID NO: 1, and the H1A domain extends from amino acid 49 to 115 of the gH protein according to SEQ ID NO: 1 (Chowdary et al., 2010). Many gH proteins do have a H1A domain, which can be identified by sequence alignment with SEQ ID NO: 1 or by structural similarity within the H1 domain as is the case for gH from Varicella Zoster Virus (human herpesvirus 3). Not every herpesvirus may have a gH with a region corresponding to amino acids 1 to 48 of the gH protein according to SEQ ID NO: 1. However, every mature gH has at least some, e.g. 1, 2 or 3 amino acids N-terminally of the H1A domain. An example is EBV, wherein only 1 residue precedes the H1A domain in the mature peptide (assuming that the H1A domain starts at the first residue visible in the Xray structure, i.e. for EBV position 19 of the gH precursor). In case of a gH in which this preceding region is very short, for example 10 or less, 5 or less, or 3 or less amino acids, it is envisaged that the insertion is behind (i.e. C-terminally of) these residues and, that, optionally, these residues are duplicated behind the insertion, i.e. between the insertion and the H1A domain.

In one embodiment of the first aspect of the invention, the herpesvirus has a reduced virulence with respect to the virulence of the wildtype virus or has a replicative capacity that is different in diseased cells vs. non-diseased cells. The term "virulence of the wildtype virus" refers to the capacity of infecting, in particular entering cells the wildtype, i.e. non-recombinant, herpesvirus has. In a particular embodiment, the reduced virulence is a reduced or even eliminated ability of binding target-cell surface receptors to which the wildtype virus binds. Such target-cell surface receptors include, for example, HVEM (synonyms used in the art: HveA and TNFRSF14) and Nectin-1 (synonyms used in the art: HveC and PVRL1), to which gD binds, heparan sulfate proteoglycans to which gB and gC bind, Myelin-associated glycoprotein MAG, paired immunoglobin-like type 2 receptor alpha (PILRalpha), DC-SIGN and non-muscle myosin heavy chain 9 MYH9/NMHC-IIA to which gB binds and ITGB3/αvβ3 integrin to which gH-gL binds, alphavbeta6-integrin and alphavbeta8-integrin to which gH binds (Gianni T, Salvioli S, Chesnokova L S, Hutt-Fletcher L M, Campadelli-Fiume G. PLoS Pathog. 2013; 9(12):e1003806). The reduced or eliminated binding can be achieved, for example, by deleting or altering the viral glycoproteins (e.g. gD, gB or gC) or parts thereof which are involved in the interaction with target-cell surface receptors.

The term "replicative capacity" refers to the number of times a herpesvirus can copy itself in an infected cell in a given time. Preferably, when the replicative capacity is different in diseased cells vs. non-diseased cells, it is higher in diseased cells than in non-diseased cells (i.e. increased for diseased cells), or lower in non-diseased cells than in diseased cells (i.e. decreased for non-diseased cells).

In a preferred embodiment, the recombinant infectious herpesvirus comprises an altered gD having reduced or no specific binding to gD's cellular ligands or it lacks gD.

In a more preferred embodiment, the herpesvirus has gD having an amino acid deletion starting at any of amino acid residues 26 to 33 and ending at any of amino acid residues 31 to 63 (preferably starting at residue 31 and ending at residue 63), and/or starting at any of amino acid residues 65 to 86 and ending at any of amino acid residues 235 to 243 (preferably starting at residue 86 and ending at residue 243) of gD according to SEQ ID NO: 4 or a corresponding region of a homologous gD. With respect to mature gD, which lacks the N-terminal 25 amino acid signal peptide, this means an amino acid deletion starting at any of amino acid residues 1 to 8 and ending at any of amino acid residues 6 to 38 (preferably starting at residue 6 and ending at residue 38), and/or starting at any of amino acid residues 40 to 61 and ending at any of amino acid residues 210 to 218 (preferably starting at residue 61 and ending at residue 218) of mature gD, respectively. Therein, the start and end residues are comprised in the deletion. The term "corresponding region of a homologous gD" refers to a region of a gD which aligns with a given region of HSV-1 gD (preferably the deletion as described above) according to SEQ ID NO: 4 when using the Smith-Waterman algorithm and the following alignment parameters: MATRIX: BLOSUM62, GAP OPEN: 10, GAP EXTEND: 0.5. In case only a part or parts of the given region of HSV-1 gD aligns with the sequence of a homologous gD using above algorithm and parameters, the term "corresponding region of a homologous gD" refers to the region which aligns with the part(s) of the given region of HSV-1 gD. In other words, in this case the deletion in the homologous gD comprises only the amino acids which align with the part(s) of the given region of HSV-1 gD. Also, in the same case, the term "corresponding region of a homologous gD" may refer to a region which is flanked by corresponding flanking sequences, wherein corresponding flanking sequences are sequences of the homologous gD which align, using above algorithm and parameters, with sequences flanking the above given region (preferably the deletion as described above) of HSV-1 gD. These flanking sequences of HSV-1 gD are at least 5, 6, 7, 8, 9, 10, 15, 20, 30, 40 or 50 amino acids long (the flanking sequence at the N-terminus of gD, i.e. N-terminal of any of amino acid residue 26 to 33 according to SEQ ID NO: 4 may be shorter, i.e. as specified but up to 25, 26, 27, 28, 29, 30, 31 or 32 amino acid residues long) and align with the sequence of a homologous gD using above algorithm and parameters. The homologous gD is preferably gD of HSV-2, gD of Chimpanzee alpha1 herpesvirus (ChHV), gD of Macacine herpesvirus 1 (MHV1), gD of Papiine herpesvirus 2 (HVP2), gD of Cercopithecine herpesvirus 1 (CeHV1), gD of Cercopithecine herpesvirus 2 (CeHV2), gD of Saimiriine herpesvirus 1 (HVS1), gD of Bovine herpes virus 1 (BoHV-1), gD of Bovine herpes virus 5 (BoHV-5), gD of Equine herpesvirus 1 (EHV-1), gD of Equine herpesvirus 3 (EHV-3), gD of Equine herpesvirus 4 (EHV-4) gD of Equine herpesvirus 8 (EHV-8), gD of Equine herpesvirus 9 (EHV-9), gD of Canine herpesvirus 1 (CHV), gD of Feline herpesvirus 1 (FHV-1), gD of Duck enteritis virus (DEV), gD of Elk herpesvirus (ElkHV), gD of Rangiferine herpesvirus (RanHV), gD of Cervid herpesvirus 1 (CerHV-1), Leporid herpesvirus 4 (LHV-4), Cervid herpesvirus 2 (CerHV-2), gD of Caprine herpesvirus 1 (CapHV-1), gD of Bubaline herpesvirus 1 (BuHV1), gD of Fruit bat alphaherpesvirus 1 (FBAHV1), gD of Macropodid herpesvirus 1 (MaHV-1), Falconid herpesvirus 1 (FaHV-1), gD of Macropodid herpesvirus 1 (MaHV-2), gD of swine pseudorabies virus (PrV), Phocid herpesvirus-1 (PhHV-1), Marek's Disease Virus (MDV), Turkey Herpesvirus (HVT), Meleagrid herpesvirus 1 (MeHV-1), gD of Gallid herpesvirus 1 (GaHV-1), gD of Gallid herpesvirus 2 (GaHV-2) or gD of Vulture herpesvirus (VHV). More preferably the homologous gD is the gD of HSV-2, gD of Chimpanzee alpha1 herpesvirus (ChHV), gD of Papiine herpesvirus 2 (HVP2), of Macacine herpesvirus 1 (MHV1), gD of Cercopithecine herpesvirus 1 (CeHV1), gD of Fruit bat alphaherpesvirus 1 (FBAHV1), gD of Cercopithecine herpesvirus 2 (CeHV2), gD of Macropodid herpesvirus 1 (MaHV-2) or gD of Saimiriine herpesvirus 1 (HVS1). Most preferably, the homologous gD is the gD of HSV-2.

In another embodiment of the first aspect of the invention, the heterologous polypeptide ligand is fused to a domain that is functionally equivalent to the N-terminus of gD and is present in a protein whose function is equivalent to HSV gD, for example gp42 of human herpesvirus 4 (EBV), BZLF2 of Macacine herpesvirus, ORF44 of callitrichine herpesvirus 3 or BZLF2 of Porcine lymphotropic herpesvirus 1.

The herpesvirus may also be attenuated, for example by deletions in or alterations of the viral genes $\gamma_1 34.5$, UL39, and/or ICP47. The term "attenuated" refers to a weakened or less virulent herpesvirus. Preferred is a conditional attenuation, wherein the attenuation affects only non-diseased cells not targeted by the herpesvirus by the retargerting according to the invention. Thus, only the diseased cells (e.g. cancer cells) to which the herpesvirus is retargeted is affected by the full virulence of the herpesvirus. A conditional attenuation can be achieved, for example, by the substitution of the promoter region of the $\gamma_1 34.5$, UL39 and/or ICP47 gene with a promoter of a human gene that is exclusively expressed in cancer cells (e.g. the survivin promoter). Further modifications for a conditional attenuation may include the substitution of regulatory regions responsible for the transcription of IE genes like the ICP-4 promoter region with promoter regions of genes exclusively expressed in diseased, e.g. cancer cells (e.g. the survivin promoter). This change will result in a replication conditional HSV, which is able to replicate in cancer cells but not in normal cells. Additional modification of the virus may include the insertion of sequence elements responsive to MicroRNAs (miRs), which are abundant in normal but not tumor cells, into the 3' untranslated region of essential HSV genes like ICP4. The result will be again a virus that is replication incompetent only in normal cells.

The term "IE genes" refers to immediate early genes, which are genes activated transiently and rapidly in response to a cellular stimulus.

In another embodiment of the first aspect of the invention, the herpesvirus comprises a heterologous polypeptide ligand fused to the N-terminus of mature gD or of a truncated gD, or inserted into gD (also referred to herein as modified gD). In a preferred embodiment, the heterologous polypeptide ligand inserted into gD is inserted C-terminally of any of amino acids 26 to 243 of gD according to SEQ ID NO: 4 (1 to 218 of mature gD) or replaces an amino acid sequence starting at any of amino acid residues 26 to 33 and ending at any of amino acid residues 31 to 63 (preferably starting at residue 31 and ending at residue 63), and/or starting at any of amino acid residues 65 to 86 and ending at any of amino acid residues 235 to 243 (preferably starting at residue 86 and ending at residue 243) of gD according to SEQ ID NO: 4 or a corresponding region of a homologous gD. Again, the term "corresponding region of a homologous gD" refers to a region of a gD which aligns with a given region of HSV-1 gD (preferably the amino acid sequence to be replaced as described above) according to SEQ ID NO: 4 when using the Smith-Waterman algorithm and the following alignment parameters: MATRIX: BLOSUM62, GAP OPEN: 10, GAP EXTEND: 0.5. In case only a part or parts of the given region of HSV-1 gD aligns with the sequence of a homologous gD using above algorithm and parameters, the term "corresponding region of a homologous gD" refers to the region which aligns with the part(s) of the given region of HSV-1 gD. In other words, in this case the sequence to be replaced in the homologous gD comprises only the amino acids which align with the part(s) of the given region of HSV-1 gD. Also, in the same case, the term "corresponding region of a homologous gD" may refer to a region which is flanked by corresponding flanking sequences, wherein corresponding flanking sequences are sequences of the homologous gD which align, using above algorithm and parameters, with sequences flanking the above given region (preferably the amino acid sequence to be replaced as described above) of HSV-1 gD. These flanking sequences of HSV-1 gD are at least 5, 6, 7, 8, 9, 10, 15, 20, 30, 40 or 50 amino acids long (the flanking sequence at the N-terminus of gD, i.e. N-terminal of any of amino acid residue 26 to 33 according to SEQ ID NO: 4 may be shorter, i.e. as specified but up to 25, 26, 27, 28, 29, 30, 31 or 32 amino acid residues long) and align with the sequence of a homologous gD using above algorithm and parameters. The homologous gD is as specified above with respect to the gD deletion.

In a preferred embodiment of the first aspect of the invention, the heterologous polypeptide ligand fused to or inserted into gH and/or gD binds to a target molecule or part thereof accessible on the surface of a cell. Preferably, it specifically binds to a molecule or part thereof accessible on the surface of a cell. The term "specifically binds" as used herein refers to a binding reaction which is determinative of the presence of said molecule in a heterogeneous population of proteins and, in particular, cells, such as in an organism, preferably a human body. As such, the specified ligand binds to its particular target molecule and does not bind in a substantial amount to other molecules present on cells or to other molecules to which the ligand may come in contact in an organism. Generally, a ligand that "specifically binds" a target molecule has an equilibrium affinity constant greater than about $10^5$ (e.g., $10^6$, $10^7$, $10^8$, $10^9$, $10^{10}$, $10^{11}$, and $10^{12}$ or more) mole/liter for that target molecule. Generally, the heterologous polypeptide ligand fused to or inserted into gH may bind to a different or to the same molecule or part thereof accessible on the surface of a cell than/as the polypeptide ligand fused to or inserted into gD. Binding to the same molecule is thought to increase the extent of binding to the one molecule, whereas binding to different molecules confers dual specificity, and provides for: 1) a maintenance of the cell specificity in the event one of the molecules is no longer present on the cell surface, for example in case of a mutated tumor cell; 2) dealing with tumor heterogeneity: tumors are heterogeneous and often a tumor specific molecule is not expressed in all tumor cells; thus dual targeting, allows the virus to enter cells using either the first or the second targeted receptor thus increasing the number of tumor cells that can be infected.

In one embodiment, the heterologous polypeptide ligand is selected from the group consisting of an antibody, an antibody derivative and an antibody mimetic. The antibody, antibody derivative or antibody mimetic may be monospecific (i.e. specific to one target molecule or part thereof accessible on the surface of a cell) or multi-specific (i.e. specific to more than one target molecule or part thereof accessible on the surface of the same or a different cell), for example bi-specific or tri-specific (see, e.g., Castoldi et al., Oncogene. 2013 Dec. 12; 32(50):5593-601; Castoldi et al., Protein Eng Des Sel. 2012 October; 25(10):551-9). The simultaneous targeting of more than one target molecule or part thereof accessible on the surface of the same cell increases specificity of the virus. The simultaneous targeting of more than one target molecule or part thereof accessible on the surface of a different cell provides for dealing with tumor heterogeneity as described above.

The term "antibody derivative" as used herein refers to a molecule comprising at least one antibody variable domain, but not having the overall structure of an antibody such as IgA, IgD, IgE, IgG, IgM, IgY or IgW, although still being capable of binding a target molecule. Said derivatives may be, but are not limited to functional (i.e. target binding, particularly specifically target binding) antibody fragments such as Fab, Fab2, scFv, Fv, or parts thereof, or other derivatives or combinations of the immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is monovalent. More preferably, the derivative is a single chain antibody, most preferably having the structure VL-peptide linker-VH or VH-peptide linker-VL.

The term "antibody mimetic" as used herein refers to organic compounds that, like antibodies, can specifically bind antigens, but that are not structurally related to antibodies. They are usually artificial peptides or proteins with a molar mass of about 3 to 20 kDa. Non-limiting examples of antibody mimetics are affibodies, affilins, affimers, affitins, anticalins, avimers, DARPins, fynomers, Kunitz domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the $10^{th}$ type III domain of fibronectin, synthetic heterobivalent or heteromultivalent ligands (Josan et al., Bioconjug Chem. 2011 22(7):1270-1278; Xu et al., PNAS 2012 109 (52) 21295-21300; Shallal et al., Bioconjug Chem. 2014 25(2) 393-405) or synthetic peptide ligands, e.g. from a (random) peptide library. Synthetic peptide ligands have non-naturally occurring amino acid sequences that function to bind a particular target molecule. Peptide ligands within the context of the present invention are generally constrained (that is, having some element of structure as, for example, the presence of amino acids which initiate a β turn or β pleated sheet, or for example, cyclized by the presence of disulfide bonded Cys residues) or unconstrained (linear) amino acid sequences of less than about 50 amino acid residues, and preferably less than about 40 amino acids residues. Of the peptide ligands less than about 40 amino acid residues, preferred are the peptide ligands of between about 10 and about 30 amino acid residues.

In one embodiment, the cell is a diseased cell. In particular, it may be a tumor cell, a chronically infected cell or a senescent cell.

In case of a tumor cell, the underlying disease is a tumor, preferably selected from the group consisting of Adrenal Cancer, Anal Cancer, Bile Duct Cancer, Bladder Cancer, Bone Cancer, Brain/CNS, Tumors, Breast Cancer, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Liver Cancer, Lung Cancer, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldnstrom Macroglobulinemia, and Wilms Tumor.

Preferred tumor diseases are HER-2-positive cancers (like breast cancer, ovary cancer, stomach cancer, lung cancer, head and neck cancer, osteosarcoma and glioblastoma multiforme), EGFR-positive cancers (like head and neck cancer, glioblastoma multiforme, non-small cell lung cancer, breast cancer, colorectal and pancreatic cancer), EGFR-vIII-positive cancers (like glioblastoma multiforme), PSMA-positive cancers (like prostate cancer), CD20+ positive lymphoma, and EBV related tumors.

In case of a chronically infected cell, the underlying disease is a chronic infectious disease, such as tuberculosis, malaria, chronic viral hepatitis (HBV, Hepatitis D virus and HCV), Acquired immune deficiency syndrome (AIDS, caused by HIV, Human Immunodeficiency Virus), or EBV related disorders: Systemic Autoimmune Diseases (Systemic Lupus Erithematosus, Rheumatoid Arthritis, and Sjogren Syndrome) and Multiple Sclerosis (MS).

In case of a senescent cell, the underlying disease is a senescence associated disease, such as (i) Rare genetic diseases called Progeroid syndromes, characterized by premature aging: Werner syndrome (WS), Bloom syndrome (BS), Rothmund-Thomson syndrome (RTS), Cockayne syndrome (CS), Xeroderma pigmentosum (XP), Trichothiodystrophy or Hutchinson-Gilford Progeria Syndrome (HGPS) or (ii) Common age related disorders: Obesity, type 2 diabetes, sarcopenia, osteoarthritis, idiopathic pulmonary fibrosis and chronic obstructive pulmonary disease, cataracts, neurodegenerative diseases, or cancer treatment related disorders.

In one embodiment, regarding the target molecule or part thereof accessible on the surface of a cell, the target molecule is a protein, a glycolipid or a glycoside. Preferably, the protein is a cellular receptor. In case of a tumor cell, it is preferred that the cell surface protein is a cancer associated antigen, such as HER2, EGFR, EGFRvIII, EGFR3 (ERBB3), MET, FAP, PSMA, CXCR4, ITGB3, CEA, CAIX, Mucins, Folate-binding protein, GD2, VEGFR1, VEGFR2, CD20, CD30, CD33, CD52, CTLA4, CD55, integrin aVI33, integrin a5131, IGF1R, EPHA3, RANKL, TRAILR1, TRAILR2, IL13Ralpha, UPAR, Tenascin, PD-1, PD-L1, Tumor-associated glycoprotein 72, Ganglioside GM2, A33, Lewis Y antigen or MUC1. In case of a senescent cell, the target molecule is any surface protein that is expressed by the senescent cell like for example CXCR2 or the IL-1 receptor.

In one embodiment, the target molecule or part thereof accessible on the surface of a diseased cell is not naturally accessible on the surface of the cell, i.e. not accessible on the surface of a non-diseased (i.e. healthy) cell of the same type and/or tissue, and preferably not accessible on the surface of any other cell of the same organism. In a related embodiment regarding chronic infections diseases the target molecule is a molecule derived from a pathogen (e.g. a virus, bacterium or parasite) that infected the cell and it is expressed on the surface of the infected cell (such as HBsAg from HBV, gp120 from HIV, E1 and E2 from HCV, LMP1 and LMP2 from EBV),In another embodiment, the heterologous polypeptide ligand fused to or inserted into gD does not bind to any molecule or part thereof accessible on the surface of a cell, but abolishes binding to natural HSV receptors. As indicated, in this embodiment, the ligand fused to or inserted into gD has the purpose of abolishing the capacity of gD to bind its natural receptors. The targeting to the target cell is accomplished by the fusion to or insertion into a different glycoprotein of the virus, in particular gH.

In another embodiment, the heterologous polypeptide ligand fused to or inserted into gH or gD binds to a heterologous molecule or part thereof accessible on the surface of a cell. The term "heterologous molecule" as used herein with respect to cells refers to a molecule that is not native to the cell. In particular, it is not produced and/or cannot be produced naturally (i.e. non-recombinantly) by the cell. Preferably, in case of a polypeptide, it is not encoded by the native (i.e. recombinantly unaltered) genome of the cell. In this embodiment, the cell targeted by the gH or gD binding to the heterologous molecule or part thereof accessible on the surface of the cell can be used for growth, i.e propagation of the virus. The manner of propagation is specific to this cell and other cells (such as cells of a patient to be treated using this herpesvirus) will not be targeted by the gH or gD binding to the heterologous molecule or part thereof.

In a further embodiment of the first aspect of the invention, the recombinant infectious herpesvirus comprises a heterologous detectable marker, preferably in an expression cassette. The term "detectable marker" as used herein refers to markers and labels commonly used in the field, for example enzymatic markers such as phosphatases and peroxidases, membrane transporters such as the NaI symporter, PET or SPEC radiotracers, or fluorescent markers. Fluorescent markers include, for example, GFP and GFP variants, e.g. mutant GFPs having a different fluorescent spectrum, RFP (e.g. mCherry RFP) and RFP variants, e.g. mutant GFPs having a different fluorescent spectrum bilirubin-inducible fluorescent protein UnaG, dsRed, eqFP611, Dronpa, TagRFPs, KFP, EosFP, Dendra, and IrisFP. For tumor visualization, the membrane transporter NaI symporter is particularly suited.

Preferably, the detectable marker is inserted into a region that does not interfere with the virus infecting the cell or with the virus multiplying in the cell or with the virus propagating. In particular, the region does not interrupt any overlapping or any transcription units (sense or anti-sense). Preferably, the detectable marker is inserted into an intergenic sequence of the herpesvirus genome, more preferably between the UL37 and the UL38, the UL3 and UL4, or the US1 and US2 intergenic sequence.

In a further embodiment of the first aspect, the recombinant infectious herpesvirus comprises one or more expression cassettes expressing one or more of the following
i) one or more therapeutic proteins, such as immunomodulators with pro-inflammatory or anti-inflammatory activity (including cytokines, preferably cytokines stimulating the immune response like GM-CSF, or IL12), antibodies, derivatives thereof or antibody mimetics, e,g, antibodies, derivatives thereof or antibody mimetics to checkpoint inhibitors (for example PDL1, PD1, CTLA4), or proteins able to modify a disease microenviroment (e.g. collagenase), in particular a tumor microenvironment,
ii) one or more heterologous or autologous antigens, epitopes/neoepitopes or string of epitopes/neoepitopes, or
iii) one or more prodrug-converting enzymes, such as valacyclovir and protein kinase of human cytomegalovirus, CYP2B1, cytosine deaminase, purine-deoxynucleoside phosphorylase, carboxylesterase, acetylcholinesterase, butyrylcholinesterase, paraoxonase, matrix metalloproteinases, alkaline phosphatase, β-Glucuronidase, valacyclovirase, plasmin, carboxypeptidase G2, penicillin amidase, β-Lactamase or β-Galactosidase (examples from Yang et al., Acta Pharmaceutica Sinica B 2011 1(3)143-159)

In a particular embodiment of the first aspect, the recombinant infectious herpesvirus has a modified gH with an amino acid sequence according to SEQ ID NO: 2 (gH as in construct R-VG803, R-VG805 and R-VG809 of the examples; scFv-HER2 between aa 23-24 of wildtype gH) or SEQ ID NO: 3 (gH as in construct R-VG811 of the examples; scFv-HER2 replacing aa 24-47 of wildtype gH), both lacking the signal sequence (residues 1-18 of SEQ ID NO: 2 and 3, respectively), or a functional variant thereof having a sequence identity of at least 80%, 85%, 90%, 95%, 96%, 97%, 98% or 99%, and optionally a modified gD with an amino acid sequence according to SEQ ID NO: 5 (gD as in construct R-LM113 of the examples, scFv HER2 replacing aa 31 to 63 of wildtype gD), SEQ ID NO: 6 (gD as in construct R-LM249 of the examples, scFv HER2 replacing aa 86-243 of wildtype gD), SEQ ID NO: 7 (gD as in construct R-VG805 of the examples, scFv EGFR replacing aa 31 to 63 of wildtype gD), SEQ ID NO: 8 (gD as in construct R-VG807 of the examples, scFv-HER2 replacing aa 31 to 63 of wildtype gD), or SEQ ID NO: 9 (gD as in construct R-VG809 of the examples, deletion of aa 31 to 63 of wildtype gD), all lacking the signal sequence (residues 1-25 of SEQ ID NOs 5-9), or a functional variant thereof having a sequence identity of at least 80%, 85%, 90%, 95%, 96%, 97%, 98% or 99%. The term "functional" in this respect, apart from gD according to SEQ ID NO: 9, means that the gH and/or gD is capable of mediating infection of a cell carrying HER2 and/or EGFR, respectively, on its surface. With respect to gD according to SEQ ID NO: 9, it means that gD with the deletion and no insertion is not capable of mediating infection of any cell, in particular via HVEM or Nectin-1.

In another particular embodiment of the first aspect, the recombinant infectious herpesvirus has a modified gH with an amino acid sequence according to SEQ ID NO: 2 or 3, wherein the gH comprises any heterologous peptide ligand as defined above in place of scFv-HER2 (particularly not scFv-HER2), or a functional variant thereof having a sequence identity of at least 80%, 85%, 90%, 95%, 96%, 97%, 98% or 99%, and optionally a modified gD with an amino acid sequence according any of SEQ ID NO: 5-9, wherein the gD of SEQ ID NO: 5-9 comprises any heterologous peptide ligand as defined above in place of that defined in these sequences (scFv-HER2 and scFv-EGFR, respectively; any means in particular not the heterologous peptide ligand defined in these sequences). The term "functional" in this respect, apart from gD according to SEQ ID NO: 9, means that the gH and/or gD is capable of mediating infection of a cell carrying a molecule on its surface to which the heterologous peptide ligand comprised in gH/gD binds. With respect to gD according to SEQ ID NO: 9, it means that gD with the deletion and no insertion is not capable of mediating infection of any cell, in particular via HVEM or Nectin-1.

In a second aspect, the present invention relates to the recombinant infectious herpesvirus of the first aspect for use in the treatment of a disease.

In a preferred embodiment, said disease is a tumor disease, a chronic infectious disease, or a senescence-associated disease.

The tumor disease is preferably selected from the group consisting of Adrenal Cancer, Anal Cancer, Bile Duct Cancer, Bladder Cancer, Bone Cancer, Brain/CNS, Tumors, Breast Cancer, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Liver Cancer, Lung Cancer, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldnstrom Macroglobulinemia, and Wilms Tumor.

Preferred tumor diseases are HER-2-positive cancers (like breast cancer, ovary cancer, stomach cancer, lung cancer, head and neck cancer, osteosarcoma and glioblastoma multiforme), EGFR-positive cancers (like head and neck cancer, glioblastoma multiforme, non-small cell lung cancer, breast cancer, colorectal and pancreatic cancer), EGFR-vIII-positive cancers (like glioblastoma multiforme), PSMA-positive cancers (like prostate cancer), CD20+ positive lymphoma, and EBV related tumors.

The chronic infectious disease is preferably selected from the group consisting of tuberculosis, malaria, chronic viral hepatitis (HBV, Hepatitis D virus and HCV), Acquired immune deficiency syndrome (AIDS, caused by HIV, Human Immunodeficiency Virus), and EBV related disorders, e.g. Systemic Autoimmune Diseases (Systemic Lupus Erithematosus, Rheumatoid Arthritis, and Sjogren Syndrome) or Multiple Sclerosis (MS).

The senescence associated disease is preferably selected from the group consisting of (i) Rare genetic diseases called Progeroid syndromes, characterized by pre-mature aging: Werner syndrome (WS), Bloom syndrome (BS), Rothmund-Thomson syndrome (RTS), Cockayne syndrome (CS), Xeroderma pigmentosum (XP), Trichothiodystrophy or Hutchinson-Gilford Progeria Syndrome (HGPS) and (ii) Common age related disorders: Obesity, type 2 diabetes, sarcopenia, osteoarthritis, idiopathic pulmonary fibrosis and chronic obstructive pulmonary disease, cataracts, neurodegenerative diseases, or cancer treatment related disorders.

In a third aspect, the present invention relates to a nucleic acid comprising the genome of the recombinant infectious herpesvirus of the first aspect or at least its heterologous polypeptide ligand fused to the N-terminus of mature gH or of a truncated gH, or inserted into gH, optionally also its heterologous polypeptide ligand fused to the N-terminus of mature gD or of a truncated, or inserted into gD. It is to be understood that the nucleic acid, in particular the genome, does preferably not encode the modified gH and optionally the modified gD as mature proteins, but as precursors including the signal sequences (residues 1-18 of SEQ ID NO: 1 and residues 1-25 of SEQ ID NO: 4). Representative examples are gH and gD according to SEQ ID NOs 2, 3 and 5-9.

In a fourth aspect, the present invention relates to a vector comprising the nucleic acid of the third aspect. Suitable vectors are known in the art and include, for example, plasmids, cosmids, artificial chromosomes (e.g. bacterial, yeast or human), bacteriophages, viral vectors (e.g. retroviruses, lentiviruses, adenoviruses, adeno-associated viruses), in particular baculovirus vector, or nano-engineered substances (e.g. ormosils).

In one embodiment, the vector is modified, in particular by a deletion, insertion and/or mutation of one or more nucleic acid residues, such that its virulence is attenuated, preferably in case of a viral vector, or that it replicates conditionally in diseased cells but not in non-diseased cells. For example, the substitution of the promoter region of the $\gamma_1 34.5$ gene with a promoter of a human gene that is exclusively expressed in cancer cells (e.g. survivin promoter), which will result in an attenuated phenotype in non-cancer cells and non-attenuated phenotype in cancer cells, is included. Further modifications may include the substitution of regulatory regions responsible for the transcription of IE genes like the ICP-4 promoter region with promoters of genes exclusively expressed in cancer cells (e.g. survivin promoter). This change will produce a replication conditional HSV, able to replicate in cancer cells but not in normal cells. Cell culture cells for propagation of the virus progeny will provide high levels of specific promoter activating proteins to allow for the production of high virus yields.

In a fifth aspect, the present invention relates to a cell comprising the recombinant infectious herpesvirus of the first aspect, the nucleic acid of the third aspect or the vector of the fourth aspect. Preferably, the cell is a cell culture cell. Suitable cell cultures and culturing techniques are well known in the art, see for example Peterson et al., Comp Immunol Microbiol Infect Dis. 1988; 11 (2): 93-8.

In a sixth aspect, the present invention relates to the recombinant infectious herpesvirus of the first aspect for use as a medicament.

In a seventh aspect, the present invention relates to a method of killing a cell using the recombinant infectious herpesvirus of the first aspect. In one embodiment, cells in a cell culture which carry the target molecule on their surface can be killed, for example to test the lytic efficacy of the recombinant infectious herpesvirus of the first aspect. In another embodiment, the cell is a diseased cell obtained from a patient, for example a tumor cell from a cancer patient, and optionally propagated. This cell is infected and thereby killed with the recombinant infectious herpesvirus of the first aspect. The successful killing of cells obtained from the patient is indicative for the cell specificity of the recombinant infectious herpesvirus of the first aspect in vivo in the patient, i.e. for the therapeutic success. In a further embodiment, also non-diseased cells may be obtained from the same patient or from a subject not suffering from the disease the patient suffers from as a control (cells not carrying the target molecule on their surface), as an indication for whether or not non-diseased cells are susceptible to infection by the recombinant infectious herpesvirus. In yet another embodiment, diseased cells comprised in a population of cells (e.g. tissue such as blood) comprising non-diseased cells and diseased cells (for example cancer cells such as leukemia cells) are killed after isolation of the population of cells from the patient (e.g. Leukapheresis). This is to obtain a population of cells free of diseased cells, e.g. blood free of diseased cells such as leukemia cells, in particular for a later transplant of the population of cells into a patient, preferably into the same patient the population of cells was isolated from. In case of blood and leukemia, for example, this method provides for re-infusion of blood free of tumor cells.

In a preferred embodiment, the method of the seventh aspect including the recited embodiments is an in vitro method.

In an eighth aspect, the present invention relates to an in vitro method for growing the recombinant infectious herpesvirus of the first aspect in cells. Suitable techniques and conditions for growing herpesvirus in cells are well known in the art, see for example Peterson et al. (Comp Immunol Microbiol Infect Dis. 1988; 11(2):93-8). In a particular embodiment, the recombinant infectious herpesvirus of the first aspect comprises a modified gH and gD as described above. Preferably, the cells in which the herpesvirus is grown in carry a target molecule to which either (i) the ligand of the modified gH or (ii) the ligand of the modified gD binds to. In case of (i), the ligand of the modified gD binds a molecule of a cell to be targeted in vivo, preferably a diseased cell in a patient, and the ligand of the modified gH binds a molecule of a cell to be targeted in cell culture; in case of (ii), the ligand of the modified gH binds a molecule of a cell to be targeted in vivo, preferably a diseased cell in a patient, and the ligand of the modified gD binds a molecule of a cell to be targeted in cell culture.

The invention is described by way of the following examples which are to be construed as merely illustrative and not limitative of the scope of the invention. It is noted that in the examples, the amino acid residue references with respect to gH relate to the precursor protein according to SEQ ID NO: 1 and the amino acid residue references with respect to gD relate to the mature protein (SEQ ID NO: 4) lacking residues 1-25).

EXAMPLES

Example 1

Construction of HSV recombinants expressing genetically modified gHs carrying a single chain antibody (scFv) directed to Her2 (scFv-HER2), without or with deletion in the HSV gene, and carrying mCherry as reporter gene.

A) R-VG803: Insertion of scFv-HER2 Between Aa 23 and 24 of HSV gH by Means of HSV-BAC and galK Recombineering.

The inventors engineered R-VG801 by insertion of the sequence encoding the trastuzumab scFv between AA 23 and 24 of gH. The starting genome was pYEBac102, which carries LOX-P-bracketed pBeloBAC sequences inserted between UL3 and UL4 of HSV-1 genome. The engineering was performed by means of galK recombineering. Briefly, the GalK cassette with homology arms to gH was amplified by means of primers gH6_galK_f ATGCG GTCCATGC-CCAGGCCATCCAAAAACCATGGGTCTGTCTGCTCA-GTCCTGTTGACA ATTAATCATCGGCA (SEQ ID NO: 10) and gH5_galK_r TCGTGGGGGTTATTAT TTTGGGCGTTGCGTGGGGTCAGGTCCACGACTG-GTCAGCACTGTCCTGCTCCTT (SEQ ID NO: 11). This cassette was electroporated in SW102 bacteria carrying pYEBac102. The recombinant clones carrying the galK cassette were selected on plates containing M63 medium (15 mM $(NH_4)_2SO_4$, 100 mM $KH_2PO_4$, 1.8 μg $FeSO_4.7H_2O$, adjusted to pH7) supplemented with 1 mg/L D-biotin, 0,2% galactose, 45 mg/L L-leucine, 1 mM $MgSO_4.7H_2O$ and 12 μg/ml chloramphenicol. In order to exclude galK false positive bacterial colonies, they were streaked also on McConkey agar base plates supplemented with 1% galactose and 12 μg/ml chloramphenicol and checked by colony PCR with primer galK_129_f ACAATCTCTGTTTGC-CAACGCATTTGG (SEQ ID NO: 28) and galK_417_r CATTGCCGCTGATCACCATGTCCACGC (SEQ ID NO: 29). Next, the trastuzumab scFv cassette bracketed by the Ser-Gly linkers described below and by homology arms to gH was amplified as two separate fragments, named fragment #1 and fragment #2, from pSG-ScFvHER2-SG. pSG-ScFvHER2-SG carries a trastuzumab scFv cassette bracketed by Ser-Gly linkers (SEQ ID NO: 12). Fragment #1 was amplified by means of primers gH23_8SG_scFv4D5_f TCGTGGGGGTTATTATTTTGGGCGTT-GCGTGGGGTCAGG TCCACGACTGGCATAGTAGTG-GCGGTGGCTCTGGATCCG (SEQ ID NO: 13) and scFv4D5_358_r GGAAACGGTTCGGATCAGCCATCGG (SEQ ID NO: 14), using pSG-ScFvHER2 as template. Fragment #2 was amplified by means of gH24_12SG_scFv4D5r ATGCGGTCCATGCCCAGGC-CATCCAAAAACCATGGGTCTGTCTGCTCAGTACCG GATCCACCGGAACCAGAGCC (SEQ ID NO: 15) and scFv4D5_315_f GGAGATCAAATCGGATATGC-CGATGG (SEQ ID NO: 16) using pSG-ScFvHER2 as template. Fragments #1 and #2 were annealed and extended to generate the scFv-HER2 cassette, bracketed by the Ser-Gly linkers and the homology arms to gH. The recombinant genome carries the scFv to HER2 bracketed by an upstream Ser-Gly linker, with sequence HSSGGGSG (SEQ ID NO: 17), and a downstream Ser-Gly linker, with sequence SSGGGSGSGGSG (SEQ ID NO: 18). The linker between $V_L$ and $V_H$ is SDMPMADPNR FRGKNLVFHS (SEQ ID NO: 19). The recombinant clones carrying the excision of the galK cassette and the insertion of the sequence of choice, exemplified by scFv-HER2, or mCherry, were selected on plates containing M63 medium (see above) supplemented with 1 mg/L D-biotin, 0.2% deoxy-2-galactose, 0.2% glycerol, 45 mg/L L-leucine, 1 mM $MgSO_4.7H_2O$ and 12 μg/ml chloramphenicol. Bacterial colonies were also checked for the presence of sequence of choice by means of colony PCR. In R-VG801 the inventors then inserted the mCherry red fluorescent protein in the UL37-UL38 intergenic region. The mCherry sequence is under the CMV promoter. First, the inventors inserted the galK cassette, amplified by means of oligonucleotides UL37/38_galK_f CCGCAGGCGTTGC-GAGTACCCCGCGTCTTCGCGGGGTGTTATACGGC-CACCCTGT TGACAATTAATCATCGGCA (SEQ ID NO: 20) and UL37/38_galK_r TCCGGACAATCCCCCGGGC-CTGGGTCCGCGAACGGGATGCCGGGACT-TAATCAGC ACTGTCCTGCTCCTT (SEQ ID NO: 21).

Subsequently, the inventors replaced the galK sequence with the promoter-mCherry cassette, amplified by means of oligonucleotides UL37/38_CMV_mcherry_f CCGCAG-GCGTTGCGAGTACCCCGCGTCTTCGCGGGGTGT-TATACGGCCACCGATG TACGGGCCAGATATACG (SEQ ID NO: 22) and UL37/38_pA_mcherry_1958_r TCCGGACAATCCCCCGGGCCTGGGTCCGC-GAACGGGATGCCGGGACTTAACCATA GAGCCCAC-CGCATCC (SEQ ID NO: 23).

B) Insertion of scFv-HER2 Between Aa 23 and 48 of HSV gH (R-VG811).

Figure 3:
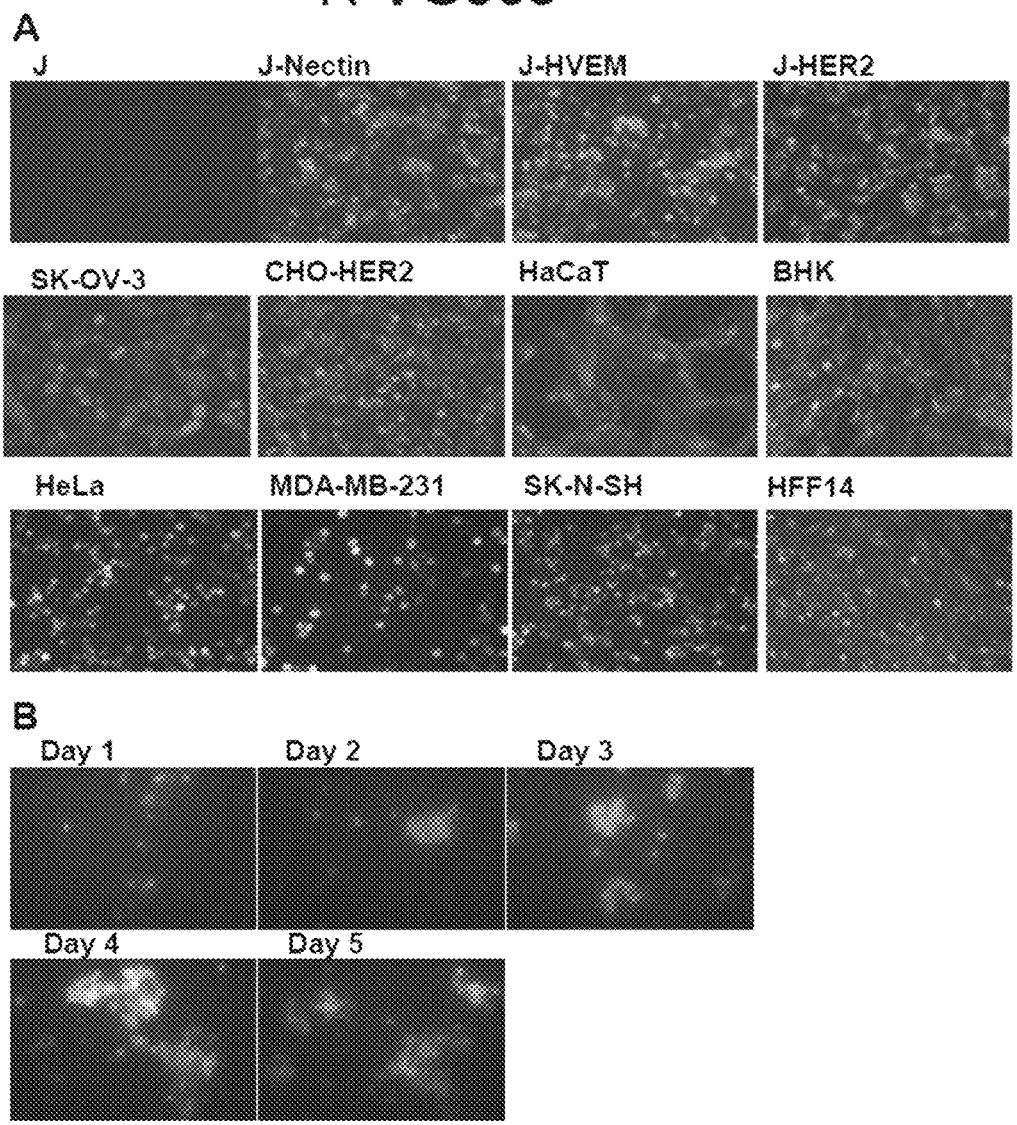

First, the inventors engineered R-VG799, by insertion of the sequence encoding the trastuzumab scFv between AA 23 and 48 of gH. The procedure was the same as described above to engineer the scFv-HER2 in gH of R-VG803, with the two following differences. First, the galK cassette was amplified by means of primers gH29_galK_f CGCGGTGGTTTTTGGGGGTCGGGGGTGTTTGGCAGCCACAGACGCCCGGTCCTGT TGACAATTAATCATCGGCA (SEQ ID NO: 24) and gH5_galK_r TCGTGGGGGTTATTATTTTGGGCGTTGCGTGGGGTCAGGTCCACGACTGGTCAGC ACTGTCCTGCTCCTT (SEQ ID NO: 25). Second, fragment #2 differed from the Fragment #2 employed to generate R-VG803, in that it was amplified by means of gH48_12SG_scFv4D5_r CCGCGCGGTGGTTTTTGGGGGTCGGGGGTGTTTGGCAGCCACAGACGCCCACCGG ATCCACCGGAACCAGAGCC (SEQ ID NO: 26) and scFv4D5_315_f GGAGATCAAATCGGATATGCCGATGG (SEQ ID NO: 27). The mCherry sequence was inserted as detailed for the construction of R-VG803.

C) R-VG809: Deletion of AA 6-38 from gD of R-VG803.

R-VG809 is identical to R-VG803 and, in addition, it carries the deletion of the sequence corresponding to AA 6-38 in gD. The starting material was the R-VG803 BAC genome. To generate the AA 6-38 deletion in gD, galK cassette flanked by homology arms to gD was amplified with primers gD5_galK_f TTGTCGTCATAGTGGGCCTCCATGGGGTCCGCGGCAAATATGCCTTGGCGCCTGT TGACAATTAATCATCGGCA (SEQ ID NO: 30) and gD39_galK_r ATCGGGAGGCTGGGGGGCTGGAACGGGTCCGGTAGGCCCGCCTGGATGTGTCAG CACTGTCCTGCTCCTT (SEQ ID NO: 31). Next, the inventors replaced galK sequence with a synthetic double-stranded oligonucleotide gD_aa5_39_f_r TTGTCGTCATAGTGGGCCTCCATGGGGTCCGCGGCAAATATGCCTTGGCGCACAT CCAGGCGGGCCTACCGGACCCGTTCCAGCCCCCCAGCCTCCCGAT (SEQ ID NO: 32).

D) R-VG805: Insertion of scFv-EGFR in Place of AA 6-38 of R-VG803 gD.

The starting material for R-VG805 was the R-VG803 BAC genome. To generate the AA 6-38 deletion in gD, galK cassette flanked by homology arms to gD was amplified with primers gD5_galK_f TTGTCGTCATAGTGGGCCTCCATGGGGTCCGCGGCAAATATGCCTTGGCGCCTGT TGACAATTAATCATCGGCA (SEQ ID NO: 33) and gD39_galK_r ATCGGGAGGCTGGGGGGCTGGAACGGGTCCGGTAGGCCCGCCTGGATGTGTCAG CACTGTCCTGCTCCTT (SEQ ID NO: 34). Next, the inventors replaced galK sequence in BAC VG804 with a scFv-EGFR cassette amplified from pTNHaa-αEGFR (kindly provided by Dr. Steve Russel, Mayo Clinic, Rochester) by means of primers BAC_LM611_f TTGTCGTCATAGTGGGCCTCCATGGGGTCCGCGGCAAATATGCCTTGGCGGCCGA GGTGCAACTGCAGCAGTC (SEQ ID NO: 35) and gD39_11SAG_EGFR_r ATCGGGAGGCTGGGGGGCTGGAACGGGTCCGGTAGGCCCGCCTGGATGTGACTT GCACTAGATGAAGCACTTCCTGCGGAAGATTTGATCTCGAGTTCTGTCCCCG (SEQ ID NO: 36). The downstream linker has the sequence SSAGSASSSAS (SEQ ID NO: 37); no upstream linker is present. The linker between VH and VL is GGGGSGGGGSGGGGS (SEQ ID NO: 38).

E) R-VG807: Insertion of scFv-HER2 in Place of AA 6-38 of R-VG803 gD.

The starting material for R-VG807 was the R-VG803 BAC genome. To generate the AA 6-38 deletion in gD, galK cassette flanked by homology arms to gD was amplified with primers gD5_galK_f TTGTCGTCATAGTGGGCCTCCATGGGGTCCGCGGCAAATATGCCTTGGCGCCTGT TGACAATTAATCATCGGCA (SEQ ID NO: 39) and gD39_galK_r ATCGGGAGGCTGGGGGGCTGGAACGGGTCCGGTAGGCCCGCCTGGATGTGTCAG CACTGTCCTGCTCCTT (SEQ ID NO: 40). Next, the inventors replaced galK sequence with scFv HER2 cassette amplified from pSG-ScFvHER2 by means of primers gD5_scFvHER2_f TTGTCGTCATAGTGGGCCTCCATGGGGTCCGCGGCAAATATGCCTTGGCGTCCGA TATCCAGATGACCCAGTCCC (SEQ ID NO: 41) and gD39_11SAG_HER2_r ATCGGGAGGCTGGGGGGCTGGAACGGGTCCGGTAGGCCCGCCTGGATGTGACTT GCACTAGATGAAGCACTTCCTGCGGAAGAGGAGACGGTGACTAGTGTTCCTTGAC C (SEQ ID NO: 42). The downstream linker has the sequence SSAGSASSSAS (SEQ ID NO: 43); no upstream linker is present. The linker between VH and VL is SDMPMADPNR FRGKNLVFHS (SEQ ID NO: 44).

To reconstitute the recombinant viruses, 500 ng of recombinant BAC DNA was transfected into SK-OV-3 cells by means of Lipofectamine 2000 (Life Technologies). Virus growth was monitored by red fluorescence. The structure of the recombinants was verified by sequencing the gH and also gD ORF for R-VG809, R-VG805 and R-VG807. Virus stocks were generated and titrated in SK-OV-3 cells, or in J-HER2 cells.

Example 2

Verification of scFv-HER2 insertion in gH of R-VG803.

Vero cells were infected with R-VG803 (3 PFU/cell), and with R-LM5 for comparison, and harvested 72 h after infection. Cell lysates were subjected to polyacrylamide gel electrophoresis, transferred to PVDF membranes, and immunoblotted with polyclonal antibody to gH. FIG. 2 shows that the chimeric scFv-HER2-gH from R-VG803 migrated with a slower electrophoretic mobility than wt-gH from R-LM5, and an apparent $M_r$ of 130 K.

Example 3

Infection assay with R-VG803, carrying the scFv-HER2 in gH, of J-HER2 cells, which express HER2 as the sole receptor.

It has previously been shown that the insertion of scFv-HER2 in gD confers to the recombinant viruses R-LM113 and R-LM249 the ability to enter cells through the HER2 receptor. To provide evidence that the insertion of scFV-HER2 in gH confers to R-VG803 the ability to enter cells through the HER2 receptor, the inventors made use of cells that express HER2 as the sole receptor. The parental J cells express no receptor for gD, hence cannot activate gD, and are not infected by wt-HSV. J-HER2 cells transgenically express HER2 as the sole receptor. As controls, the inventors included J-nectin and J-HVEM cells, which transgenically express Nectin 1 or HVEM as receptors and are infected by wt-HSV, and human and animal cells which express the human or animal HVEM/Nectin 1 orthologs, namely the keratinocytic HaCaT, the neuronal SK-N-SH, the cancer HeLa, MDA-MB-231, the human fibroblastic HFF14, the hamster BHK cells, as well as the ovary cancer SK-OV-3 cells which express HER2 plus HVEM/Nectin 1. As shown in FIG. 3 A, R-VG803 infected J-HER2 cells. The infection of J-Nectin 1, J-HVEM, and of human and animal cells with R-VG803 (FIG. 3 A) was not surprising, inasmuch as R-VG803 encodes a wt-gD. The inventors further report that R-VG803 can perform cell-to-cell spread in J-HER2 cells. Cells were infected at 0.01 PFU/cell, and monitored daily. At day 1 infection involved single cells. In the following days infection involved clusters of cells, progressively larger in size (FIG. 3 B).

Figure 4:
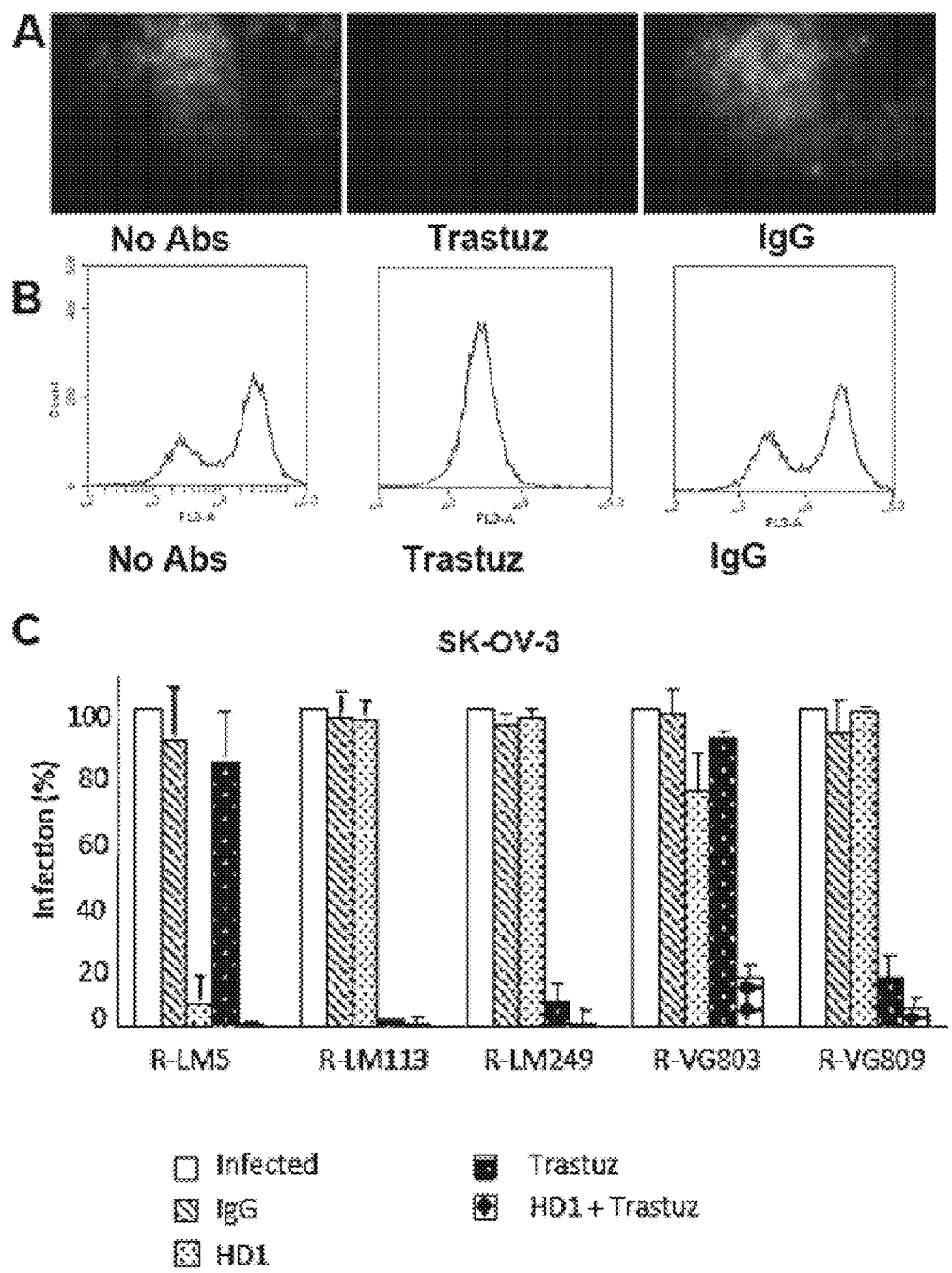

To prove that entry of R-VG803 into J-HER2 cells occurs through HER2 as the cellular receptor, and to investigate the role of gD in the entry pathway of R-VG803 into SK-OV-3 cells, the inventors first confirmed that infection occurs through the HER2 receptor. J-HER2 cells were infected with R-VG803 in the presence of trastuzumab, the MAb to HER2 from which the scFv-HER2 was derived. Trastuzumab blocked the infection of J-HER2 cells with R-VG803, as detected by fluorescence microscopy (FIG. 4 A) and quantified by fluorescent activated cell sorter (FACS) (FIG. 4 B). This validates the conclusion that the retargeted R-VG803 uses HER2 as the portal of entry in J-HER2 cells. The finding that R-VG803 can make use of HER2 as receptor provides evidence that the tropism of HSV can be modified by engineering a heterologous ligand in gH. Furthermore, the infection of the gH-retargeted HSV R-VG803 into J-HER2 cells can take place in cells which lack a gD receptor, i.e. in conditions in which gD is physically present in R-VG803 virions, but functionally ablated since it cannot be activated by its cognate receptors and cannot transmit the activation to gH. The inventors conclude that infection of R-VG803 does not necessitate of a gD with functional receptor-binding sites. Next, the inventors analysed the receptor usage in SK-OV-3 cells that express both sets of receptors, HER2 and nectin1/HVEM. The question was whether one receptor was preferentially used over the other, or each one was used alternatively. SK-OV-3 cells were infected with R-VG803, in the presence of MAb to HER2 (trastuzumab), MAb HD1, or both. The controls were R-LM5, which carries a wt-gD and the other genomic modifications present in R-VG803, R-LM249 and R-LM113, namely the insertion of the BAC sequences and the insertion of the GFP marker. R-LM249 is a HSV retargeted to HER2 by means of scFv-HER2 insertion in the deletion of AA 61-218 of gD. R-LM113 is a HSV retargeted to HER2 by means of scFv-HER2 insertion in the deletion of AA 6-38 of mature gD. R-VG809 was also included (see example 4). FIG. 4 C shows that MAb to HER2 or HD1 exerted almost no inhibition on R-VG803 when given singly, but practically abolished infection when given together. Thus, R-VG803 can use alternatively HER2 or Nectin1/HVEM to infect SK-OV-3 cells. Usage of one or the other portals of entry by R-VG803 depends on the spectrum of receptors displayed by the cells. As expected, the fully retargeted R-LM249 and R-LM113 exhibit a pathway of entry dependent on HER2. Infection with R-VG809 is also inhibited by trastuzumab, either alone or in combination with MAb HD1, leading to the conclusion that this recombinant is retargeted to HER2 by means of gH, and detargeted from nectin1/HVEM in consequence of the AA 6-38 deletion in mature gD.

Example 4

Genetic engineering of the R-VG809 recombinant retargeted to HER2 by insertion of scFV-HER2 in gH and detargeted from gD receptors by deletion of the gD sequence encoding AA 6-38.

Figure 5:
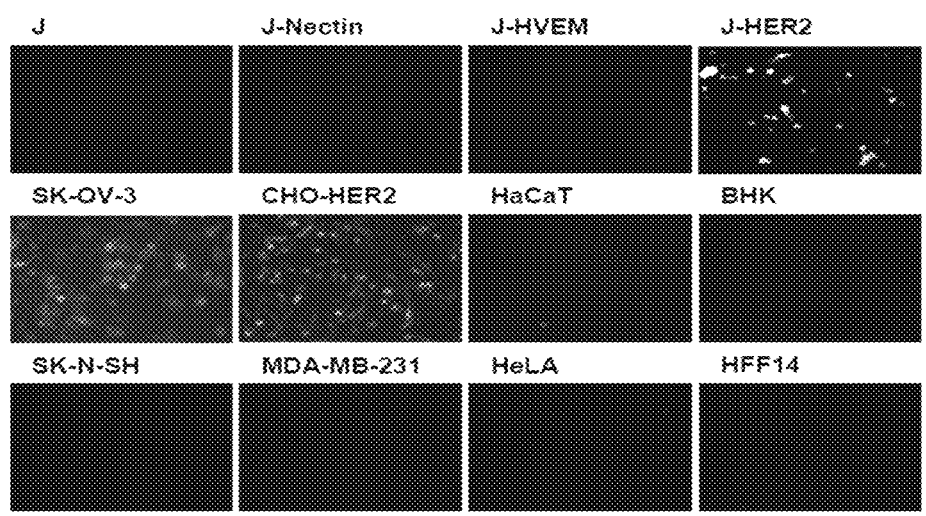

The inventors engineered a recombinant carrying the scFv-HER2 in gH and the deletion of portions of receptors' binding sites from gD. The two major receptors of gD are Nectin 1 and HVEM. The binding site of HVEM in gD maps to AA 1-32. The binding site of Nectin 1 in mature gD is more widespread and includes the Ig-folded core and portions located between AA 35-38, 199-201, 214-217, 219-221. The inventors deleted from R-VG803 mature gD the AA 6-38 region, i.e. the same region which was previously deleted from R-LM113, a HSV retargeted to HER2 by insertion of the scFv-HER2 between AA 5 and 39 of mature gD. The deletion removes the entire HVEM binding site and some residues implicated in the interaction with Nectin 1, which include the Ig-folded core and portions located between AA 35-38, 199-201, 214-217, 219-221. Even though a few AA implicated in the interaction with Nectin 1 were deleted, R-LM113 was shown to be detargeted from Nectin 1 and from HVEM, the recombinant is detargeted from both HVEM and Nectin 1. The recombinant virus named R-VG809 failed to infect not only J-HVEM cells, but also J-Nectin 1 cells, as well as the human HaCaT, SK-N-SH, MDA-MB-231, HeLA, HFF14 cells, the hamster BHK cells. It maintained the ability to infect efficiently J-HER2 and SK-OV-3 cells (FIG. 5). R-VG809 tropism is strikingly different from that of R-VG803 (compare FIG. 5 with FIG. 3A). The inventors conclude that R-VG809 infection via the HER2-retargeted gH does not require the binding sites for HVEM and for Nectin 1 in gD, and, consequently, the receptor-mediated gD activation. In summary, R-VG809 exhibits a fully redirected tropism, retargeted to the HER2 receptor via gH and detargeted from gD receptors. Its pathway of entry in SK-OV-3 cells is shown in FIG. 4. It can be seen that, in contrast to the entry of R-VG803, the entry of R-VG809 into SK-OV-3 cells was inhibited by trastuzumab alone, indicating that it is entirely through the HER2 receptor.

Example 5

Genetic engineering of the R-VG805 recombinant retargeted to HER2 by insertion of scFv-HER2 in gH and retargeted to EGFR by insertion of scFv-EGFR in place of AA 6-38 region of mature gD. Double Retargeting to two different receptors of choice plus detargeting from gD receptors.

Figure 6:
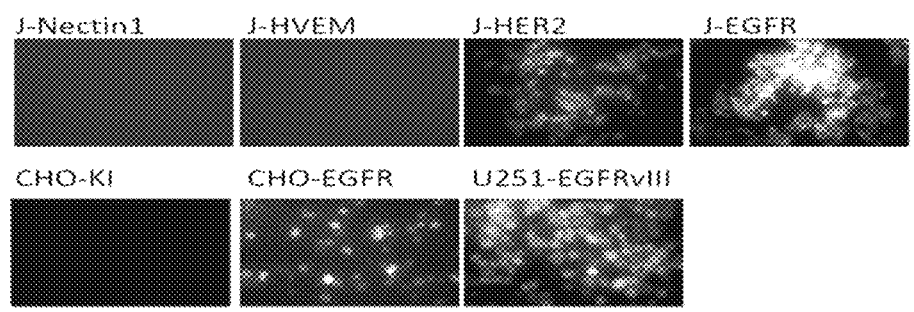
Figure 7:
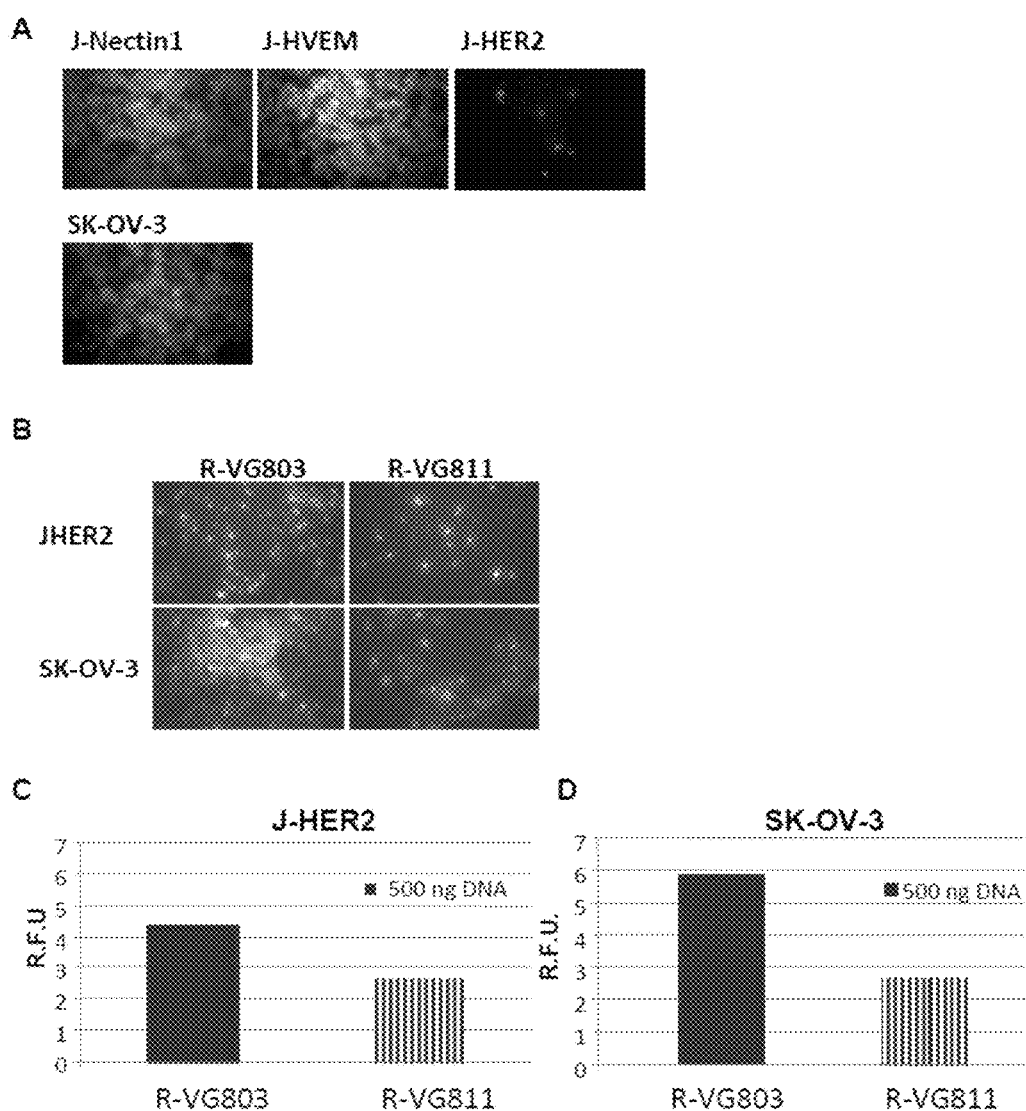
Figure 8:
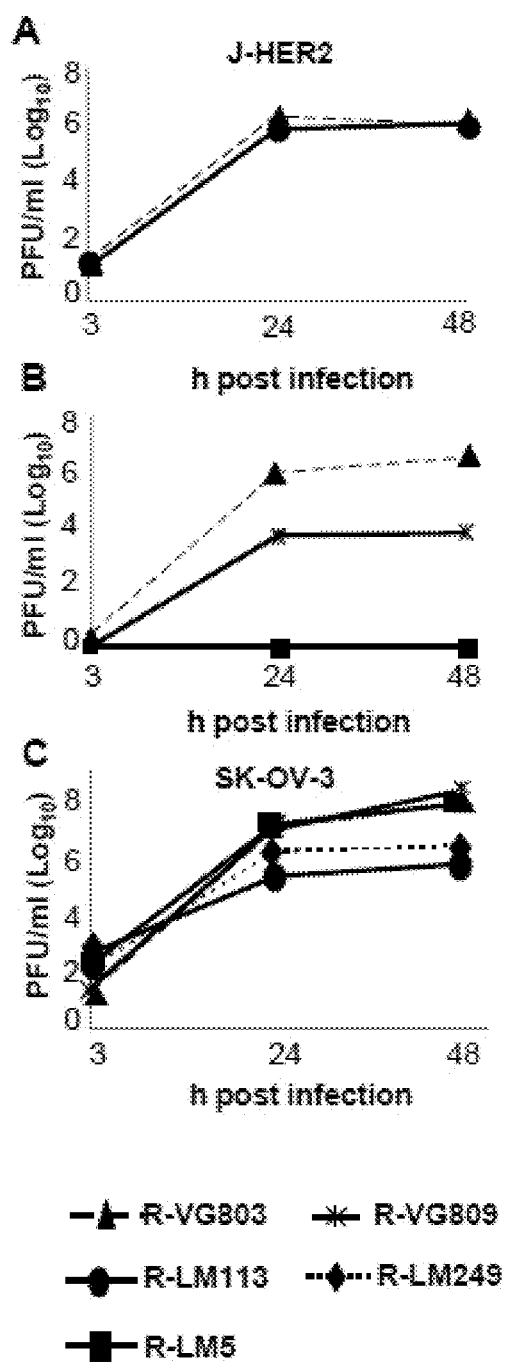
Figure 9:
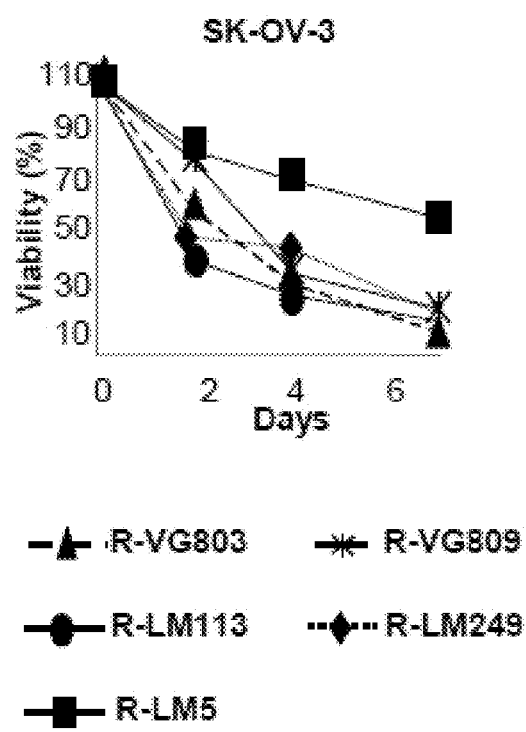

The inventors engineered a HSV recombinant simultaneously retargeted to HER2, by insertion of scFv-HER2 in gH, and to EGFR, by insertion of scFv-EGFR in place of AA 6-38 region of mature gD. Briefly, R-VG803 was modified so as to replace the endogenous AA 6-38 region of mature gD with the scFv to EGFR, herein named scFv-EGFR. The recombinant virus named R-VG805 was indeed retargeted to HER2 by means of gH, detargeted from Nectin 1 and HVEM, because of the deletion of the AA 6-38 region in mature gD, and retargeted to EGFR because of the insertion of the scFv to EGFR in place of AA 6-38 of mature gD (FIG. 6). The inventors note that the insertion of scFV-EFGR retargets R-VG805 also the EGFR-vIII, a variant of EGFR that carries a deletion (FIG. 6). This EGFR variant is highly expressed in human glioblastoma. These results show that it is possible to engineer a HSV recombinant with a double retargeting to two different receptors of choice.

Example 6

Genetic engineering of the R-VG807 recombinant double-retargeted to HER2 by insertion of scFv-HER2 in gH and by insertion of scFv-HER2 in place of AA 6-38 region of mature gD. Double retargeting to a same receptor of choice plus detargeting from gD receptors.

The inventors engineered a HSV recombinant retargeted to HER2 both by insertion of scFv-HER2 in gH and by insertion of scFv-HER2 in place of AA 6-38 region of mature gD. Briefly, R-VG803 was modified so as to replace the endogenous AA 6-38 region of mature gD with the scFv-HER2. The recombinant virus named R-VG807 is double-retargeted to HER2, and detargeted from Nectin 1 and HVEM, because of the deletion of the AA 6-38 region in mature gD.

Example 7

Study on the insertion site for scFv-HER2 in gH. Deletion of sequence encoding AA 24-47.

The inventors investigated whether insertion of the scFv-HER2 can be coupled with the deletion of N-terminal portion of gH. The deleted portion was the sequence coding for AA 24-47 of gH. This sequence was replaced with scFv-HER2. The resulting recombinant was named R-VG811. FIG. 7 shows that R-VG811 infected J-HER2 cells. Thus the insertion of the scFv-HER2 can be coupled with a deletion in gH, at least up to AA 48. This indicates that the site of insertion can be C-terminal to AA 18 and N-terminal of any AA between AA 19 and AA 48. Atanasiu et al. (MBio. 2013 Feb. 26; 4(2). pii: e00046-13. doi: 10.1128/mBio.00046-13) proposed that "gHΔ48/gL has an intermediate structure on the pathway leading to full regulatory activation and suggested that a key step in the pathway of fusion is the conversion of gH/gL to an activated state by receptor-bound gD; this activated gH/gL resembles gHΔ48/gL". On the basis of results by Atanasiu, obtained in the cell-cell fusion assay and not in the virion-cell entry, an expert in the art might hypothesize that deletion of the sequence AA 24-47 in gH, and its replacement with scFv-HER2 might lead to virus more prone to fuse with cell membrane, and therefore capable of enhanced infection relative to R-VG803. The inventors transfected the DNA-BAC of R-VG811 and, for comparison of R-VG803 in SK-OV-3 and in J-HER2 cells and determined the extent of virus infection/formation through the amount of cells expressing the mCherry marker. FIG. 7 B-D compare the amount of infected cells obtained upon transfection of R-VG811 or of R-VG803 DNA in J-HER2 or SK-OV-3 cells. The quantification of the experiment is shown in FIG. 7 C-D. Overall, the efficiency of infectious virus production was lower with R-VG811 than with R-VG803, indicating that the deletion of AA at the N-ter of gH, up to AA 48 reduces the infectious capacity of the recombinants. Thus, the results of Atanasiu et al. were not predictive of the behaviour of a HSV recombinant carrying the insertion of scFv-HER2 in place of the deleted AA 24-47 endogenous gH sequences.

Example 8

Extent of replication of recombinants.

The inventors compared the extent of replication of R-VG803 and R-VG809 to that of two recombinants, R-LM113 and R-LM249, that are retargeted to HER2 through the insertion of scFv-HER2 in gD. Replication was measured in J-HER2 cells, which express the HER2 as the receptor, and in SK-OV-3 cells, which express HER2 and Nectin1/HVEM as receptors. Cells were infected at 0.1 PFU/cell or 0.01 PFU/ml, and harvested 3, 24, 48 h after infection. The results in FIG. 8 show that R-VG803 and R-VG809 replicated as efficiently as R-LM113 or R-LM249, or even more efficiently in SK-OV-3 cells.

Example 9

Ability of R-VG803 and R-VG809 to kill HER2-positive cancer cells.

As a measure of the ability of R-VG803 or R-VG809 to kill cells, the inventors performed a cytotoxicity test, by means of AlamarBlue, for HER2 positive SK-OV-3 cells. The wt HSV R-LM5, and the retargeted R-LM113 and R-LM249 were included for comparison. FIG. 9 shows that cytotoxicity caused by R-VG803, by R-VG809 were very similar to those caused by R-LM113 or R-LM249.

The invention claimed is:

1. A recombinant infectious herpesvirus comprising a heterologous polypeptide ligand inserted into mature glycoprotein H (gH)
   (i) between amino acid 23 and amino acid 24 of the gH according to SEQ ID NO: 1 or a corresponding region of a homologous gH, or
   (ii) within the region starting at amino acid 116 and ending at amino acid 136 of the gH according to SEQ ID NO: 1 or a corresponding region of a homologous gH.

2. The recombinant infectious herpesvirus of claim 1, wherein one or more gH amino acids of the N-terminal region are deleted.

3. The recombinant infectious herpesvirus of claim 1, wherein said herpesvirus has a reduced virulence compared to a wildtype, or has a higher replicative capacity in diseased cells than in non-diseased cells.

4. The recombinant infectious herpesvirus of claim 1, comprising an altered glycoprotein D (gD) having reduced specific binding to gD's cellular ligands compared to wild-type gD or having no specific binding to gD's cellular ligands, or which lacks gD.

5. A recombinant infectious herpesvirus comprising a heterologous polypeptide ligand fused to the N-terminus of mature glycoprotein H (gH) or of a truncated gH, or inserted into gH, and further comprising a heterologous polypeptide ligand fused to the N-terminus of mature gD or of a truncated gD, or inserted into gD.

6. The recombinant infectious herpesvirus of claim 1, further comprising a heterologous detectable marker and/or one or more expression cassettes expressing one or more of the following
   i) one or more therapeutic proteins,
   ii) one or more heterologous or autologous antigens, epitopes/neoepitopes or string of epitopes/neoepitopes, or
   iii) one or more prodrug-converting enzymes.

7. The recombinant infectious herpesvirus of claim 1, wherein the heterologous polypeptide ligand fused to or inserted into gH binds to a molecule or part thereof accessible on the surface of a cell.

8. The recombinant infectious herpesvirus of claim 1 for use in medicine.

9. The recombinant infectious herpesvirus of claim 4, comprising an altered glycoprotein D (gD), wherein gD has an amino acid deletion starting at any of amino acid residues 26 to 33 and ending at any of amino acid residues 31 to 63, and/or starting at any of amino acid residues 65 to 86 and ending at any of amino acid residues 235 to 243 of the gD according to SEQ ID NO: 4 or a corresponding region of a homologous gD.

10. The recombinant infectious herpesvirus of claim 7, wherein the cell is a diseased cell.

11. The recombinant infectious herpesvirus of claim 5, wherein the heterologous polypeptide ligand is inserted within the N-terminal region starting at any one of amino acids 19 to 23 and ending at any one of amino acids 48 to 88 or starting at amino acid 116 and ending at amino acid 136 of the gH according to SEQ ID NO: 1 or a corresponding region of a homologous gH.

12. The recombinant infectious herpesvirus of claim 5, wherein the heterologous polypeptide ligand is inserted N-terminally of the H1A domain of gH.

13. The recombinant infectious herpesvirus of claim 5, comprising an altered glycoprotein D (gD) having reduced specific binding to gD's cellular ligands compared to wild-type gD or having no specific binding to gD's cellular ligands, or which lacks gD.

14. The recombinant infectious herpesvirus of claim 5, comprising an altered glycoprotein D (gD), wherein gD has an amino acid deletion starting at any of amino acid residues 26 to 33 and ending at any of amino acid residues 31 to 63, and/or starting at any of amino acid residues 65 to 86 and ending at any of amino acid residues 235 to 243 of the gD according to SEQ ID NO: 4 or a corresponding region of a homologous gD.

15. The recombinant infectious herpesvirus of claim 5, wherein one or more gH amino acids of the N-terminal region are deleted.

16. The recombinant infectious herpesvirus of claim 5, wherein said herpesvirus has a reduced virulence compared to the wildtype, or has a higher replicative capacity in diseased cells than in non-diseased cells.

17. The recombinant infectious herpesvirus of claim 5, further comprising a heterologous detectable marker and/or one or more expression cassettes expressing one or more of the following:
   i) one or more therapeutic proteins;
   ii) one or more heterologous or autologous antigens, epitopes/neoepitopes or string of epitopes/neoepitopes; or
   iii) one or more prodrug-converting enzymes.

18. The recombinant infectious herpesvirus of claim 5, wherein the heterologous polypeptide ligand fused to or inserted into gH and/or gD binds to a molecule or part thereof accessible on the surface of a cell.

19. The recombinant infectious herpesvirus of claim 18, wherein the cell is a diseased cell.

20. The recombinant infectious herpesvirus of claim 5 for use in medicine.

21. A recombinant infectious herpesvirus comprising a heterologous polypeptide ligand fused to the N-terminus of mature glycoprotein H (gH) or of a truncated gH, or inserted into gH, and further comprising an altered glycoprotein D (gD), wherein gD has an amino acid deletion starting at any of amino acid residues 26 to 33 and ending at any of amino acid residues 31 to 63, and/or starting at any of amino acid residues 65 to 86 and ending at any of amino acid residues 235 to 243 of the gD according to SEQ ID NO: 4 or a corresponding region of a homologous gD.

22. The recombinant infectious herpesvirus of claim 21, wherein the heterologous polypeptide ligand is inserted within the N-terminal region starting at any one of amino acids 19 to 23 and ending at any one of amino acids 48 to 88 or starting at amino acid 116 and ending at amino acid 136 of the gH according to SEQ ID NO: 1 or a corresponding region of a homologous gH.

23. The recombinant infectious herpesvirus of claim 21, wherein the heterologous polypeptide ligand is inserted N-terminally of the H1A domain of gH.

24. The recombinant infectious herpesvirus of claim 21, wherein one or more gH amino acids of the N-terminal region are deleted.

25. The recombinant infectious herpesvirus of claim 21, wherein said herpesvirus has a reduced virulence compared to the wildtype, or has a higher replicative capacity in diseased cells than in non-diseased cells.

26. The recombinant infectious herpesvirus of claim 21, comprising a heterologous polypeptide ligand fused to the N-terminus of mature gD or of a truncated gD, or inserted into gD.

27. The recombinant infectious herpesvirus of claim 21, further comprising a heterologous detectable marker and/or one or more expression cassettes expressing one or more of the following:
   i) one or more therapeutic proteins;
   ii) one or more heterologous or autologous antigens, epitopes/

SEQUENCE LISTING

```
<160> NUMBER OF SEQ ID NOS: 44

<210> SEQ ID NO 1
<211> LENGTH: 838
<212> TYPE: PRT
<213> ORGANISM: HSV-1

<400> SEQUENCE: 1

Met Gly Asn Gly Leu Trp Phe Val Gly Val Ile Ile Leu Gly Val Ala
1               5                   10                  15

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
        35                  40                  45

Arg Leu Trp Leu Pro Asn Thr Pro Asp Pro Gln Lys Pro Pro Arg Gly
    50                  55                  60

Phe Leu Ala Pro Pro Asp Glu Leu Asn Leu Thr Thr Ala Ser Leu Pro
65                  70                  75                  80

Leu Leu Arg Trp Tyr Glu Glu Arg Phe Cys Phe Val Leu Val Thr Thr
                85                  90                  95
```

```
Ala Glu Phe Pro Arg Asp Pro Gly Gln Leu Leu Tyr Ile Pro Lys Thr
                100                 105                 110

Tyr Leu Leu Gly Arg Pro Pro Asn Ala Ser Leu Pro Ala Pro Thr Thr
            115                 120                 125

Val Glu Pro Thr Ala Gln Pro Pro Ser Val Ala Pro Leu Lys Gly
        130                 135                 140

Leu Leu Tyr Asn Pro Val Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
            180                 185                 190

Pro Pro Pro Arg Pro Pro Val Gly Ala Arg Arg His Pro Thr Thr Glu
        195                 200                 205

Leu Asp Ile Thr His Leu His Asn Ala Ser Thr Thr Trp Leu Ala Thr
210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
            260                 265                 270

Gly Leu Val Ile Ser Met His Asp Ser Pro Val Glu Val Met Val
        275                 280                 285

Val Pro Ala Gly Gln Thr Leu Asp Arg Val Gly Asp Pro Ala Asp Glu
290                 295                 300

Asn Pro Pro Gly Ala Leu Pro Gly Pro Pro Gly Pro Arg Tyr Arg
305                 310                 315                 320

Val Phe Val Leu Gly Ser Leu Thr Arg Ala Asp Asn Gly Ser Ala Leu
                325                 330                 335

Asp Ala Leu Arg Arg Val Gly Gly Tyr Pro Glu Glu Gly Thr Asn Tyr
            340                 345                 350

Ala Gln Phe Leu Ser Arg Ala Tyr Ala Glu Phe Phe Ser Gly Asp Ala
        355                 360                 365

Gly Ala Glu Gln Gly Pro Arg Pro Pro Leu Phe Trp Arg Leu Thr Gly
370                 375                 380

Leu Leu Ala Thr Ser Gly Phe Ala Phe Val Asn Ala Ala His Ala Asn
385                 390                 395                 400

Gly Ala Val Cys Leu Ser Asp Leu Leu Gly Phe Leu Ala His Ser Arg
                405                 410                 415

Ala Leu Ala Gly Leu Ala Ala Arg Gly Ala Ala Gly Cys Ala Ala Asp
            420                 425                 430

Ser Val Phe Phe Asn Val Ser Val Leu Asp Pro Thr Ala Arg Leu Gln
        435                 440                 445

Leu Glu Ala Arg Leu Gln His Leu Val Ala Glu Ile Leu Glu Arg Glu
450                 455                 460

Gln Ser Leu Ala Leu His Ala Leu Gly Tyr Gln Leu Ala Phe Val Leu
465                 470                 475                 480

Asp Ser Pro Ser Ala Tyr Asp Ala Val Ala Pro Ser Ala Ala His Leu
                485                 490                 495

Ile Asp Ala Leu Tyr Ala Glu Phe Leu Gly Gly Arg Val Leu Thr Thr
            500                 505                 510
```

-continued

Pro Val Val His Arg Ala Leu Phe Tyr Ala Ser Ala Val Leu Arg Gln
515                 520                 525

Pro Phe Leu Ala Gly Val Pro Ser Ala Val Gln Arg Glu Arg Ala Arg
        530                 535                 540

Arg Ser Leu Leu Ile Ala Ser Ala Leu Cys Thr Ser Asp Val Ala Ala
545                 550                 555                 560

Ala Thr Asn Ala Asp Leu Arg Thr Ala Leu Ala Arg Ala Asp His Gln
                565                 570                 575

Lys Thr Leu Phe Trp Leu Pro Asp His Phe Ser Pro Cys Ala Ala Ser
            580                 585                 590

Leu Arg Phe Asp Leu Asp Glu Ser Val Phe Ile Leu Asp Ala Leu Ala
        595                 600                 605

Gln Ala Thr Arg Ser Glu Thr Pro Val Glu Val Leu Ala Gln Gln Thr
610                 615                 620

His Gly Leu Ala Ser Thr Leu Thr Arg Trp Ala His Tyr Asn Ala Leu
625                 630                 635                 640

Ile Arg Ala Phe Val Pro Glu Ala Ser His Arg Cys Gly Gly Gln Ser
                645                 650                 655

Ala Asn Val Glu Pro Arg Ile Leu Val Pro Ile Thr His Asn Ala Ser
            660                 665                 670

Tyr Val Val Thr His Ser Pro Leu Pro Arg Gly Ile Gly Tyr Lys Leu
        675                 680                 685

Thr Gly Val Asp Val Arg Arg Pro Leu Phe Leu Thr Tyr Leu Thr Ala
690                 695                 700

Thr Cys Glu Gly Ser Thr Arg Asp Ile Glu Ser Lys Arg Leu Val Arg
705                 710                 715                 720

Thr Gln Asn Gln Arg Asp Leu Gly Leu Val Gly Ala Val Phe Met Arg
                725                 730                 735

Tyr Thr Pro Ala Gly Glu Val Met Ser Val Leu Leu Val Asp Thr Asp
            740                 745                 750

Asn Thr Gln Gln Gln Ile Ala Ala Gly Pro Thr Glu Gly Ala Pro Ser
        755                 760                 765

Val Phe Ser Ser Asp Val Pro Ser Thr Ala Leu Leu Leu Phe Pro Asn
770                 775                 780

Gly Thr Val Ile His Leu Leu Ala Phe Asp Thr Gln Pro Val Ala Ala
785                 790                 795                 800

Ile Ala Pro Gly Phe Leu Ala Ser Ala Leu Gly Val Val Met Ile
                805                 810                 815

Thr Ala Ala Leu Ala Gly Ile Leu Lys Val Leu Arg Thr Ser Val Pro
820                 825                 830

Phe Phe Trp Arg Arg Glu
        835

<210> SEQ ID NO 2
<211> LENGTH: 1105
<212> TYPE: PRT
<213> ORGANISM: Artificial Sequence
<220> FEATURE:
<223> OTHER INFORMATION: gH as in construct R-VG803, R-VG805 and R-VG809

<400> SEQUENCE: 2

Met Gly Asn Gly Leu Trp Phe Val Gly Val Ile Ile Leu Gly Val Ala
1               5                   10                  15

Trp Gly Gln Val His Asp Trp His Ser Ser Gly Gly Ser Gly Ser
            20                  25                  30

```
Asp Ile Gln Met Thr Gln Ser Pro Ser Ser Leu Ser Ala Ser Val Gly
         35                  40                  45

Asp Arg Val Thr Ile Thr Cys Arg Ala Ser Gln Asp Val Asn Thr Ala
 50                  55                  60

Val Ala Trp Tyr Gln Gln Lys Pro Gly Lys Ala Pro Lys Leu Leu Ile
 65                  70                  75                  80

Tyr Ser Ala Ser Phe Leu Tyr Ser Gly Val Pro Ser Arg Phe Ser Gly
                 85                  90                  95

Ser Arg Ser Gly Thr Asp Phe Thr Leu Thr Ile Ser Ser Leu Gln Pro
             100                 105                 110

Glu Asp Phe Ala Thr Tyr Tyr Cys Gln Gln His Tyr Thr Thr Pro Pro
         115                 120                 125

Thr Phe Gly Gln Gly Thr Lys Val Glu Ile Lys Ser Asp Met Pro Met
     130                 135                 140

Ala Asp Pro Asn Arg Phe Arg Gly Lys Asn Leu Val Phe His Ser Glu
145                 150                 155                 160

Val Gln Leu Val Glu Ser Gly Gly Leu Val Gln Pro Gly Gly Ser
                 165                 170                 175

Leu Arg Leu Ser Cys Ala Ala Ser Gly Phe Asn Ile Lys Asp Thr Tyr
             180                 185                 190

Ile His Trp Val Arg Gln Ala Pro Gly Lys Gly Leu Glu Trp Val Ala
         195                 200                 205

Arg Ile Tyr Pro Thr Asn Gly Tyr Thr Arg Tyr Ala Asp Ser Val Lys
     210                 215                 220

Gly Arg Phe Thr Ile Ser Ala Asp Thr Ser Lys Asn Thr Ala Tyr Leu
225                 230                 235                 240

Gln Met Asn Ser Leu Arg Ala Glu Asp Thr Ala Val Tyr Tyr Cys Ser
                 245                 250                 255

Arg Trp Gly Gly Asp Gly Phe Tyr Ala Met Asp Tyr Trp Gly Gln Gly
             260                 265                 270

Thr Leu Val Thr Val Ser Ser Ser Gly Gly Ser Gly Ser Gly Gly
         275                 280                 285

Ser Gly Thr Glu Gln Thr Asp Pro Trp Phe Leu Asp Gly Leu Gly Met
     290                 295                 300

Asp Arg Met Tyr Trp Arg Asp Thr Asn Thr Gly Arg Leu Trp Leu Pro
305                 310                 315                 320

Asn Thr Pro Asp Pro Gln Lys Pro Arg Gly Phe Leu Ala Pro Pro
                 325                 330                 335

Asp Glu Leu Asn Leu Thr Thr Ala Ser Leu Pro Leu Leu Arg Trp Tyr
             340                 345                 350

Glu Glu Arg Phe Cys Phe Val Leu Val Thr Thr Ala Glu Phe Pro Arg
         355                 360                 365

Asp Pro Gly Gln Leu Leu Tyr Ile Pro Lys Thr Tyr Leu Leu Gly Arg
     370                 375                 380

Pro Pro Asn Ala Ser Leu Pro Ala Pro Thr Thr Val Glu Pro Thr Ala
385                 390                 395                 400

Gln Pro Pro Pro Ser Val Ala Pro Leu Lys Gly Leu Leu Tyr Asn Pro
                 405                 410                 415

Val Ala Ser Val Leu Leu Arg Ser Arg Ala Trp Val Thr Phe Ser Ala
             420                 425                 430

Val Pro Asp Pro Glu Ala Leu Thr Phe Pro Arg Gly Asp Asn Val Ala
         435                 440                 445
```

```
Thr Ala Ser His Pro Ser Gly Pro Arg Asp Thr Pro Pro Arg Pro
450                 455                 460

Pro Val Gly Ala Arg Arg His Pro Thr Thr Glu Leu Asp Ile Thr His
465                 470                 475                 480

Leu His Asn Ala Ser Thr Thr Trp Leu Ala Thr Arg Gly Leu Leu Arg
                485                 490                 495

Ser Pro Gly Arg Tyr Val Tyr Phe Ser Pro Ser Ala Ser Thr Trp Pro
                500                 505                 510

Val Gly Ile Trp Thr Thr Gly Glu Leu Val Leu Gly Cys Asp Ala Ala
            515                 520                 525

Leu Val Arg Ala Arg Tyr Gly Arg Glu Phe Met Gly Leu Val Ile Ser
530                 535                 540

Met His Asp Ser Pro Pro Val Glu Val Met Val Pro Ala Gly Gln
545                 550                 555                 560

Thr Leu Asp Arg Val Gly Asp Pro Ala Asp Glu Asn Pro Pro Gly Ala
                565                 570                 575

Leu Pro Gly Pro Pro Gly Gly Pro Arg Tyr Arg Val Phe Val Leu Gly
                580                 585                 590

Ser Leu Thr Arg Ala Asp Asn Gly Ser Ala Leu Asp Ala Leu Arg Arg
                595                 600                 605

Val Gly Gly Tyr Pro Glu Glu Gly Thr Asn Tyr Ala Gln Phe Leu Ser
610                 615                 620

Arg Ala Tyr Ala Glu Phe Phe Ser Gly Asp Ala Gly Ala Glu Gln Gly
625                 630                 635                 640

Pro Arg Pro Pro Leu Phe Trp Arg Leu Thr Gly Leu Leu Ala Thr Ser
                645                 650                 655

Gly Phe Ala Phe Val Asn Ala Ala His Ala Asn Gly Ala Val Cys Leu
                660                 665                 670

Ser Asp Leu Leu Gly Phe Leu Ala His Ser Arg Ala Leu Ala Gly Leu
                675                 680                 685

Ala Ala Arg Gly Ala Ala Gly Cys Ala Ala Asp Ser Val Phe Phe Asn
690                 695                 700

Val Ser Val Leu Asp Pro Thr Ala Arg Leu Gln Leu Glu Ala Arg Leu
705                 710                 715                 720

Gln His Leu Val Ala Glu Ile Leu Glu Arg Glu Gln Ser Leu Ala Leu
                725                 730                 735

His Ala Leu Gly Tyr Gln Leu Ala Phe Val Leu Asp Ser Pro Ser Ala
                740                 745                 750

Tyr Asp Ala Val Ala Pro Ser Ala Ala His Leu Ile Asp Ala Leu Tyr
                755                 760                 765

Ala Glu Phe Leu Gly Gly Arg Val Leu Thr Thr Pro Val Val His Arg
                770                 775                 780

Ala Leu Phe Tyr Ala Ser Ala Val Leu Arg Gln Pro Phe Leu Ala Gly
785                 790                 795                 800

Val Pro Ser Ala Val Gln Arg Glu Arg Ala Arg Ser Leu Leu Ile
                805                 810                 815

Ala Ser Ala Leu Cys Thr Ser Asp Val Ala Ala Thr Asn Ala Asp
                820                 825                 830

Leu Arg Thr Ala Leu Ala Arg Ala Asp His Gln Lys Thr Leu Phe Trp
                835                 840                 845

Leu Pro Asp His Phe Ser Pro Cys Ala Ala Ser Leu Arg Phe Asp Leu
                850                 855                 860
```

```
Asp Glu Ser Val Phe Ile Leu Asp Ala Leu Ala Gln Ala Thr Arg Ser
865                 870                 875                 880

Glu Thr Pro Val Glu Val Leu Ala Gln Gln Thr His Gly Leu Ala Ser
            885                 890                 895

Thr Leu Thr Arg Trp Ala His Tyr Asn Ala Leu Ile Arg Ala Phe Val
            900                 905                 910

Pro Glu Ala Ser His Arg Cys Gly Gly Gln Ser Ala Asn Val Glu Pro
            915                 920                 925

Arg Ile Leu Val Pro Ile Thr His Asn Ala Ser Tyr Val Val Thr His
930                 935                 940

Ser Pro Leu Pro Arg Gly Ile Gly Tyr Lys Leu Thr Gly Val Asp Val
945                 950                 955                 960

Arg Arg Pro Leu Phe Leu Thr Tyr Leu Thr Ala Thr Cys Glu Gly Ser
            965                 970                 975

Thr Arg Asp Ile Glu Ser Lys Arg Leu Val Arg Thr Gln Asn Gln Arg
            980                 985                 990

Asp Leu Gly Leu Val Gly Ala Val Phe Met Arg Tyr Thr Pro Ala Gly
            995                 1000                1005

Glu Val Met Ser Val Leu Leu Val Asp Thr Asp Asn Thr Gln Gln
    1010                1015                1020

Gln Ile Ala Ala Gly Pro Thr Glu Gly Ala Pro Ser Val Phe Ser
    1025                1030                1035

Ser Asp Val Pro Ser Thr Ala Leu Leu Leu Phe Pro Asn Gly Thr
    1040                1045                1050

Val Ile His Leu Leu Ala Phe Asp Thr Gln Pro Val Ala Ala Ile
    1055                1060                1065

Ala Pro Gly Phe Leu Ala Ala Ser Ala Leu Gly Val Val Met Ile
    1070                1075                1080

Thr Ala Ala Leu Ala Gly Ile Leu Lys Val Leu Arg Thr Ser Val
    1085                1090                1095

Pro Phe Phe Trp Arg Arg Glu
    1100                1105

<210> SEQ ID NO 3
<211> LENGTH: 1081
<212> TYPE: PRT
<213> ORGANISM: Artificial Sequence
<220> FEATURE:
<223> OTHER INFORMATION: gH as in construct R-VG811

<400> SEQUENCE: 3

Met Gly Asn Gly Leu Trp Phe Val Gly Val Ile Ile Leu Gly Val Ala
1               5                   10                  15

Trp Gly Gln Val His Asp Trp His Ser Ser Gly Gly Ser Gly Ser
            20                  25                  30

Asp Ile Gln Met Thr Gln Ser Pro Ser Ser Leu Ser Ala Ser Val Gly
            35                  40                  45

Asp Arg Val Thr Ile Thr Cys Arg Ala Ser Gln Asp Val Asn Thr Ala
        50                  55                  60

Val Ala Trp Tyr Gln Gln Lys Pro Gly Lys Ala Pro Lys Leu Leu Ile
65                  70                  75                  80

Tyr Ser Ala Ser Phe Leu Tyr Ser Gly Val Pro Ser Arg Phe Ser Gly
                85                  90                  95

Ser Arg Ser Gly Thr Asp Phe Thr Leu Thr Ile Ser Ser Leu Gln Pro
            100                 105                 110
```

```
Glu Asp Phe Ala Thr Tyr Tyr Cys Gln Gln His Tyr Thr Pro Pro
            115                 120                 125

Thr Phe Gly Gln Gly Thr Lys Val Glu Ile Lys Ser Asp Met Pro Met
130                 135                 140

Ala Asp Pro Asn Arg Phe Arg Gly Lys Asn Leu Val Phe His Ser Glu
145                 150                 155                 160

Val Gln Leu Val Glu Ser Gly Gly Leu Val Gln Pro Gly Gly Ser
            165                 170                 175

Leu Arg Leu Ser Cys Ala Ala Ser Gly Phe Asn Ile Lys Asp Thr Tyr
                180                 185                 190

Ile His Trp Val Arg Gln Ala Pro Gly Lys Gly Leu Glu Trp Val Ala
        195                 200                 205

Arg Ile Tyr Pro Thr Asn Gly Tyr Thr Arg Tyr Ala Asp Ser Val Lys
    210                 215                 220

Gly Arg Phe Thr Ile Ser Ala Asp Thr Ser Lys Asn Thr Ala Tyr Leu
225                 230                 235                 240

Gln Met Asn Ser Leu Arg Ala Glu Asp Thr Ala Val Tyr Tyr Cys Ser
                245                 250                 255

Arg Trp Gly Gly Asp Gly Phe Tyr Ala Met Asp Tyr Trp Gly Gln Gly
        260                 265                 270

Thr Leu Val Thr Val Ser Ser Ser Gly Gly Ser Gly Ser Gly Gly
    275                 280                 285

Ser Gly Gly Arg Leu Trp Leu Pro Asn Thr Pro Asp Pro Gln Lys Pro
        290                 295                 300

Pro Arg Gly Phe Leu Ala Pro Pro Asp Glu Leu Asn Leu Thr Ala
305                 310                 315                 320

Ser Leu Pro Leu Leu Arg Trp Tyr Glu Glu Arg Phe Cys Phe Val Leu
                325                 330                 335

Val Thr Thr Ala Glu Phe Pro Arg Asp Pro Gly Gln Leu Leu Tyr Ile
        340                 345                 350

Pro Lys Thr Tyr Leu Leu Gly Arg Pro Pro Asn Ala Ser Leu Pro Ala
    355                 360                 365

Pro Thr Thr Val Glu Pro Thr Ala Gln Pro Pro Ser Val Ala Pro
370                 375                 380

Leu Lys Gly Leu Leu Tyr Asn Pro Val Ala Ser Val Leu Leu Arg Ser
385                 390                 395                 400

Arg Ala Trp Val Thr Phe Ser Ala Val Pro Asp Pro Glu Ala Leu Thr
                405                 410                 415

Phe Pro Arg Gly Asp Asn Val Ala Thr Ala Ser His Pro Ser Gly Pro
        420                 425                 430

Arg Asp Thr Pro Pro Arg Pro Val Gly Ala Arg His Pro
    435                 440                 445

Thr Thr Glu Leu Asp Ile Thr His Leu His Asn Ala Ser Thr Thr Trp
        450                 455                 460

Leu Ala Thr Arg Gly Leu Leu Arg Ser Pro Gly Arg Tyr Val Tyr Phe
465                 470                 475                 480

Ser Pro Ser Ala Ser Thr Trp Pro Val Gly Ile Trp Thr Thr Gly Glu
                485                 490                 495

Leu Val Leu Gly Cys Asp Ala Ala Leu Val Arg Ala Arg Tyr Gly Arg
        500                 505                 510

Glu Phe Met Gly Leu Val Ile Ser Met His Asp Ser Pro Pro Val Glu
    515                 520                 525
```

-continued

Val Met Val Val Pro Ala Gly Gln Thr Leu Asp Arg Val Gly Asp Pro
530                535                540

Ala Asp Glu Asn Pro Pro Gly Ala Leu Pro Gly Pro Gly Gly Pro
545                550                555                560

Arg Tyr Arg Val Phe Val Leu Gly Ser Leu Thr Arg Ala Asp Asn Gly
                565                570                575

Ser Ala Leu Asp Ala Leu Arg Arg Val Gly Gly Tyr Pro Glu Glu Gly
            580                585                590

Thr Asn Tyr Ala Gln Phe Leu Ser Arg Ala Tyr Ala Glu Phe Phe Ser
        595                600                605

Gly Asp Ala Gly Ala Glu Gln Gly Pro Arg Pro Pro Leu Phe Trp Arg
    610                615                620

Leu Thr Gly Leu Leu Ala Thr Ser Gly Phe Ala Phe Val Asn Ala Ala
625                630                635                640

His Ala Asn Gly Ala Val Cys Leu Ser Asp Leu Leu Gly Phe Leu Ala
                645                650                655

His Ser Arg Ala Leu Ala Gly Leu Ala Ala Arg Gly Ala Ala Gly Cys
            660                665                670

Ala Ala Asp Ser Val Phe Phe Asn Val Ser Val Leu Asp Pro Thr Ala
        675                680                685

Arg Leu Gln Leu Glu Ala Arg Leu Gln His Leu Val Ala Glu Ile Leu
    690                695                700

Glu Arg Glu Gln Ser Leu Ala Leu His Ala Leu Gly Tyr Gln Leu Ala
705                710                715                720

Phe Val Leu Asp Ser Pro Ser Ala Tyr Asp Ala Val Ala Pro Ser Ala
                725                730                735

Ala His Leu Ile Asp Ala Leu Tyr Ala Glu Phe Leu Gly Gly Arg Val
            740                745                750

Leu Thr Thr Pro Val Val His Arg Ala Leu Phe Tyr Ala Ser Ala Val
        755                760                765

Leu Arg Gln Pro Phe Leu Ala Gly Val Pro Ser Ala Val Gln Arg Glu
    770                775                780

Arg Ala Arg Arg Ser Leu Leu Ile Ala Ser Ala Leu Cys Thr Ser Asp
785                790                795                800

Val Ala Ala Ala Thr Asn Ala Asp Leu Arg Thr Ala Leu Ala Arg Ala
                805                810                815

Asp His Gln Lys Thr Leu Phe Trp Leu Pro Asp His Phe Ser Pro Cys
            820                825                830

Ala Ala Ser Leu Arg Phe Asp Leu Asp Glu Ser Val Phe Ile Leu Asp
        835                840                845

Ala Leu Ala Gln Ala Thr Arg Ser Glu Thr Pro Val Glu Val Leu Ala
    850                855                860

Gln Gln Thr His Gly Leu Ala Ser Thr Leu Thr Arg Trp Ala His Tyr
865                870                875                880

Asn Ala Leu Ile Arg Ala Phe Val Pro Glu Ala Ser His Arg Cys Gly
                885                890                895

Gly Gln Ser Ala Asn Val Glu Pro Arg Ile Leu Val Pro Ile Thr His
            900                905                910

Asn Ala Ser Tyr Val Val Thr His Ser Pro Leu Pro Arg Gly Ile Gly
        915                920                925

Tyr Lys Leu Thr Gly Val Asp Val Arg Arg Pro Leu Phe Leu Thr Tyr
    930                935                940

-continued

```
Leu Thr Ala Thr Cys Glu Gly Ser Thr Arg Asp Ile Glu Ser Lys Arg
945                 950                 955                 960

Leu Val Arg Thr Gln Asn Gln Arg Asp Leu Gly Leu Val Gly Ala Val
            965                 970                 975

Phe Met Arg Tyr Thr Pro Ala Gly Glu Val Met Ser Val Leu Leu Val
            980                 985                 990

Asp Thr Asp Asn Thr Gln Gln Gln Ile Ala Ala Gly Pro Thr Glu Gly
        995                1000                1005

Ala Pro Ser Val Phe Ser Ser Asp Val Pro Ser Thr Ala Leu Leu
    1010                1015                1020

Leu Phe Pro Asn Gly Thr Val Ile His Leu Leu Ala Phe Asp Thr
    1025                1030                1035

Gln Pro Val Ala Ala Ile Ala Pro Gly Phe Leu Ala Ala Ser Ala
    1040                1045                1050

Leu Gly Val Val Met Ile Thr Ala Ala Leu Ala Gly Ile Leu Lys
    1055                1060                1065

Val Leu Arg Thr Ser Val Pro Phe Phe Trp Arg Arg Glu
    1070                1075                1080

<210> SEQ ID NO 4
<211> LENGTH: 394
<212> TYPE: PRT
<213> ORGANISM: HSV-1

<400> SEQUENCE: 4

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala Val Leu Glu Arg Ala Cys Arg Ser Val Leu Leu
                85                  90                  95

Asn Ala Pro Ser Glu Ala Pro Gln Ile Val Arg Gly Ala Ser Glu Asp
            100                 105                 110

Val Arg Lys Gln Pro Tyr Asn Leu Thr Ile Ala Trp Phe Arg Met Gly
        115                 120                 125

Gly Asn Cys Ala Ile Pro Ile Thr Val Met Glu Tyr Thr Glu Cys Ser
    130                 135                 140

Tyr Asn Lys Ser Leu Gly Ala Cys Pro Ile Arg Thr Gln Pro Arg Trp
145                 150                 155                 160

Asn Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Lys Gly Ser Cys Lys Tyr Ala Leu Pro Leu Arg Ile Pro Pro
    210                 215                 220

Ser Ala Cys Leu Ser Pro Gln Ala Tyr Gln Gln Gly Val Thr Val Asp
225                 230                 235                 240
```

```
Ser Ile Gly Met Leu Pro Arg Phe Ile Pro Glu Asn Gln Arg Thr Val
            245                 250                 255

Ala Val Tyr Ser Leu Lys Ile Ala Gly Trp His Gly Pro Lys Ala Pro
        260                 265                 270

Tyr Thr Ser Thr Leu Leu Pro Pro Glu Leu Ser Glu Thr Pro Asn Ala
    275                 280                 285

Thr Gln Pro Glu Leu Ala Pro Glu Asp Pro Glu Asp Ser Ala Leu Leu
290                 295                 300

Glu Asp Pro Val Gly Thr Val Ala Pro Gln Ile Pro Asn Trp His
305                 310                 315                 320

Ile Pro Ser Ile Gln Asp Ala Ala Thr Pro Tyr His Pro Pro Ala Thr
                325                 330                 335

Pro Asn Asn Met Gly Leu Ile Ala Gly Ala Val Gly Gly Ser Leu Leu
            340                 345                 350

Ala Ala Leu Val Ile Cys Gly Ile Val Tyr Trp Met Arg Arg Arg Thr
        355                 360                 365

Gln Lys Ala Pro Lys Arg Ile Arg Leu Pro His Ile Arg Glu Asp Asp
    370                 375                 380

Gln Pro Ser Ser His Gln Pro Leu Phe Tyr
385                 390

<210> SEQ ID NO 5
<211> LENGTH: 621
<212> TYPE: PRT
<213> ORGANISM: Artificial Sequence
<220> FEATURE:
<223> OTHER INFORMATION: gD as in R-LM113

<400> SEQUENCE: 5

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Glu Asn
            20                  25                  30

Ser Asp Ile Gln Met Thr Gln Ser Pro Ser Ser Leu Ser Ala Ser Val
        35                  40                  45

Gly Asp Arg Val Thr Ile Thr Cys Arg Ala Ser Gln Asp Val Asn Thr
    50                  55                  60

Ala Val Ala Trp Tyr Gln Gln Lys Pro Gly Lys Ala Pro Lys Leu Leu
65                  70                  75                  80

Ile Tyr Ser Ala Ser Phe Leu Tyr Ser Gly Val Pro Ser Arg Phe Ser
                85                  90                  95

Gly Ser Arg Ser Gly Thr Asp Phe Thr Leu Thr Ile Ser Ser Leu Gln
            100                 105                 110

Pro Glu Asp Phe Ala Thr Tyr Tyr Cys Gln Gln His Tyr Thr Thr Pro
        115                 120                 125

Pro Thr Phe Gly Gln Gly Thr Lys Val Glu Ile Lys Ser Asp Met Pro
    130                 135                 140

Met Ala Asp Pro Asn Arg Phe Arg Gly Lys Asn Leu Val Phe His Ser
145                 150                 155                 160

Glu Val Gln Leu Val Glu Ser Gly Gly Gly Leu Val Gln Pro Gly Gly
                165                 170                 175

Ser Leu Arg Leu Ser Cys Ala Ala Ser Gly Phe Asn Ile Lys Asp Thr
            180                 185                 190

Tyr Ile His Trp Val Arg Gln Ala Pro Gly Lys Gly Leu Glu Trp Val
        195                 200                 205
```

```
Ala Arg Ile Tyr Pro Thr Asn Gly Tyr Thr Arg Tyr Ala Asp Ser Val
    210                 215                 220

Lys Gly Arg Phe Thr Ile Ser Ala Asp Thr Ser Lys Asn Thr Ala Tyr
225                 230                 235                 240

Leu Gln Met Asn Ser Leu Arg Ala Glu Asp Thr Ala Val Tyr Tyr Cys
                245                 250                 255

Ser Arg Trp Gly Gly Asp Gly Phe Tyr Ala Met Asp Tyr Trp Gly Gln
            260                 265                 270

Gly Thr Leu Val Thr Val Ser Ser Gly Gly Gly Ser Gly Ser Gly
                275                 280                 285

Gly Ser His Ile Gln Ala Gly Leu Pro Asp Pro Phe Gln Pro Pro Ser
        290                 295                 300

Leu Pro Ile Thr Val Tyr Tyr Ala Val Leu Glu Arg Ala Cys Arg Ser
305                 310                 315                 320

Val Leu Leu Asn Ala Pro Ser Glu Ala Pro Gln Ile Val Arg Gly Ala
                325                 330                 335

Ser Glu Asp Val Arg Lys Gln Pro Tyr Asn Leu Thr Ile Ala Trp Phe
            340                 345                 350

Arg Met Gly Gly Asn Cys Ala Ile Pro Ile Thr Val Met Glu Tyr Thr
        355                 360                 365

Glu Cys Ser Tyr Asn Lys Ser Leu Gly Ala Cys Pro Ile Arg Thr Gln
    370                 375                 380

Pro Arg Trp Asn Tyr Tyr Asp Ser Phe Ser Ala Val Ser Glu Asp Asn
385                 390                 395                 400

Leu Gly Phe Leu Met His Ala Pro Ala Phe Glu Thr Ala Gly Thr Tyr
                405                 410                 415

Leu Arg Leu Val Lys Ile Asn Asp Trp Thr Glu Ile Thr Gln Phe Ile
            420                 425                 430

Leu Glu His Arg Ala Lys Gly Ser Cys Lys Tyr Ala Leu Pro Leu Arg
        435                 440                 445

Ile Pro Pro Ser Ala Cys Leu Ser Pro Gln Ala Tyr Gln Gln Gly Val
    450                 455                 460

Thr Val Asp Ser Ile Gly Met Leu Pro Arg Phe Ile Pro Glu Asn Gln
465                 470                 475                 480

Arg Thr Val Ala Val Tyr Ser Leu Lys Ile Ala Gly Trp His Gly Pro
                485                 490                 495

Lys Ala Pro Tyr Thr Ser Thr Leu Leu Pro Pro Glu Leu Ser Glu Thr
            500                 505                 510

Pro Asn Ala Thr Gln Pro Glu Leu Ala Pro Glu Asp Pro Glu Asp Ser
        515                 520                 525

Ala Leu Leu Glu Asp Pro Val Gly Thr Val Ala Pro Gln Ile Pro Pro
    530                 535                 540

Asn Trp His Ile Pro Ser Ile Gln Asp Ala Ala Thr Pro Tyr His Pro
545                 550                 555                 560

Pro Ala Thr Pro Asn Asn Met Gly Leu Ile Ala Gly Ala Val Gly Gly
                565                 570                 575

Ser Leu Leu Ala Ala Leu Val Ile Cys Gly Ile Val Tyr Trp Met Arg
            580                 585                 590

Arg Arg Thr Gln Lys Ala Pro Lys Arg Ile Arg Leu Pro His Ile Arg
        595                 600                 605

Glu Asp Asp Gln Pro Ser Ser His Gln Pro Leu Phe Tyr
    610                 615                 620
```

```
<210> SEQ ID NO 6
<211> LENGTH: 503
<212> TYPE: PRT
<213> ORGANISM: Artificial Sequence
<220> FEATURE:
<223> OTHER INFORMATION: gD as in R-LM249

<400> SEQUENCE: 6
```

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asp Pro Phe Gln Pro Pro Ser Leu Pro Ile
65                  70                  75                  80

Thr Val Tyr Tyr Ala His Ser Ser Gly Gly Ser Gly Ser Asp Ile
                85                  90                  95

Gln Met Thr Gln Ser Pro Ser Ser Leu Ser Ala Ser Val Gly Asp Arg
            100                 105                 110

Val Thr Ile Thr Cys Arg Ala Ser Gln Asp Val Asn Thr Ala Val Ala
        115                 120                 125

Trp Tyr Gln Gln Lys Pro Gly Lys Ala Pro Lys Leu Leu Ile Tyr Ser
    130                 135                 140

Ala Ser Phe Leu Tyr Ser Gly Val Pro Ser Arg Phe Ser Gly Ser Arg
145                 150                 155                 160

Ser Gly Thr Asp Phe Thr Leu Thr Ile Ser Ser Leu Gln Pro Glu Asp
                165                 170                 175

Phe Ala Thr Tyr Tyr Cys Gln Gln His Tyr Thr Thr Pro Pro Thr Phe
            180                 185                 190

Gly Gln Gly Thr Lys Val Glu Ile Lys Ser Asp Met Pro Met Ala Asp
        195                 200                 205

Pro Asn Arg Phe Arg Gly Lys Asn Leu Val Phe His Ser Glu Val Gln
    210                 215                 220

Leu Val Glu Ser Gly Gly Gly Leu Val Gln Pro Gly Gly Ser Leu Arg
225                 230                 235                 240

Leu Ser Cys Ala Ala Ser Gly Phe Asn Ile Lys Asp Thr Tyr Ile His
                245                 250                 255

Trp Val Arg Gln Ala Pro Gly Lys Gly Leu Glu Trp Val Ala Arg Ile
            260                 265                 270

Tyr Pro Thr Asn Gly Tyr Thr Arg Tyr Ala Asp Ser Val Lys Gly Arg
        275                 280                 285

Phe Thr Ile Ser Ala Asp Thr Ser Lys Asn Thr Ala Tyr Leu Gln Met
    290                 295                 300

Asn Ser Leu Arg Ala Glu Asp Thr Ala Val Tyr Tyr Cys Ser Arg Trp
305                 310                 315                 320

Gly Gly Asp Gly Phe Tyr Ala Met Asp Tyr Trp Gly Gln Gly Thr Leu
                325                 330                 335

Val Thr Val Ser Ser Ser Gly Gly Ser Gly Ser Gly Ser Gly
            340                 345                 350

Met Leu Pro Arg Phe Ile Pro Glu Asn Gln Arg Thr Val Ala Val Tyr
        355                 360                 365

Ser Leu Lys Ile Ala Gly Trp His Gly Pro Lys Ala Pro Tyr Thr Ser
370                 375                 380

Thr Leu Leu Pro Pro Glu Leu Ser Glu Thr Pro Asn Ala Thr Gln Pro
385                 390                 395                 400

Glu Leu Ala Pro Glu Asp Pro Glu Asp Ser Ala Leu Leu Glu Asp Pro
                405                 410                 415

Val Gly Thr Val Ala Pro Gln Ile Pro Pro Asn Trp His Ile Pro Ser
            420                 425                 430

Ile Gln Asp Ala Ala Thr Pro Tyr His Pro Pro Ala Thr Pro Asn Asn
            435                 440                 445

Met Gly Leu Ile Ala Gly Ala Val Gly Gly Ser Leu Leu Ala Ala Leu
450                 455                 460

Val Ile Cys Gly Ile Val Tyr Trp Met Arg Arg Thr Gln Lys Ala
465                 470                 475                 480

Pro Lys Arg Ile Arg Leu Pro His Ile Arg Glu Asp Asp Gln Pro Ser
                485                 490                 495

Ser His Gln Pro Leu Phe Tyr
            500

<210> SEQ ID NO 7
<211> LENGTH: 615
<212> TYPE: PRT
<213> ORGANISM: Artificial Sequence
<220> FEATURE:
<223> OTHER INFORMATION: gD as in R-VG805

<400> SEQUENCE: 7

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Ala Glu
            20                  25                  30

Val Gln Leu Gln Gln Ser Gly Ala Glu Leu Val Lys Pro Gly Ala Ser
        35                  40                  45

Val Lys Leu Ser Cys Lys Ala Ser Gly Tyr Thr Phe Thr Ser His Trp
    50                  55                  60

Met His Trp Val Lys Gln Arg Ala Gly Gln Gly Leu Glu Trp Ile Gly
65                  70                  75                  80

Glu Phe Asn Pro Ser Asn Gly Arg Thr Asn Tyr Asn Glu Lys Phe Lys
                85                  90                  95

Ser Lys Ala Thr Leu Thr Val Asp Lys Ser Ser Ser Thr Ala Tyr Met
            100                 105                 110

Gln Leu Ser Ser Leu Thr Ser Glu Asp Ser Ala Val Tyr Tyr Cys Ala
        115                 120                 125

Ser Arg Asp Tyr Asp Tyr Asp Gly Arg Tyr Phe Asp Tyr Trp Gly Gln
    130                 135                 140

Gly Thr Thr Val Thr Val Ser Ser Gly Gly Gly Gly Ser Gly Gly Gly
145                 150                 155                 160

Gly Ser Gly Gly Gly Gly Ser Asp Ile Glu Leu Thr Gln Ser Pro Ala
                165                 170                 175

Ile Met Ser Ala Ser Pro Gly Glu Lys Val Thr Met Thr Cys Ser Ala
            180                 185                 190

Ser Ser Ser Val Thr Tyr Met Tyr Trp Tyr Gln Gln Lys Pro Gly Ser
        195                 200                 205

Ser Pro Arg Leu Leu Ile Tyr Asp Thr Ser Asn Leu Ala Ser Gly Val
    210                 215                 220

```
Pro Val Arg Phe Ser Gly Ser Gly Ser Gly Thr Ser Tyr Ser Leu Thr
225                 230                 235                 240

Ile Ser Arg Met Glu Ala Glu Asp Ala Ala Thr Tyr Tyr Cys Gln Gln
            245                 250                 255

Trp Ser Ser His Ile Phe Thr Phe Gly Ser Gly Thr Glu Leu Glu Ile
                260                 265                 270

Lys Ser Ser Ala Gly Ser Ala Ser Ser Ser Ala Ser His Ile Gln Ala
            275                 280                 285

Gly Leu Pro Asp Pro Phe Gln Pro Pro Ser Leu Pro Ile Thr Val Tyr
        290                 295                 300

Tyr Ala Val Leu Glu Arg Ala Cys Arg Ser Val Leu Leu Asn Ala Pro
305                 310                 315                 320

Ser Glu Ala Pro Gln Ile Val Arg Gly Ala Ser Glu Asp Val Arg Lys
                325                 330                 335

Gln Pro Tyr Asn Leu Thr Ile Ala Trp Phe Arg Met Gly Gly Asn Cys
                340                 345                 350

Ala Ile Pro Ile Thr Val Met Glu Tyr Thr Glu Cys Ser Tyr Asn Lys
            355                 360                 365

Ser Leu Gly Ala Cys Pro Ile Arg Thr Gln Pro Arg Trp Asn Tyr Tyr
        370                 375                 380

Asp Ser Phe Ser Ala Val Ser Glu Asp Asn Leu Gly Phe Leu Met His
385                 390                 395                 400

Ala Pro Ala Phe Glu Thr Ala Gly Thr Tyr Leu Arg Leu Val Lys Ile
                405                 410                 415

Asn Asp Trp Thr Glu Ile Thr Gln Phe Ile Leu Glu His Arg Ala Lys
            420                 425                 430

Gly Ser Cys Lys Tyr Ala Leu Pro Leu Arg Ile Pro Pro Ser Ala Cys
        435                 440                 445

Leu Ser Pro Gln Ala Tyr Gln Gln Gly Val Thr Val Asp Ser Ile Gly
        450                 455                 460

Met Leu Pro Arg Phe Ile Pro Glu Asn Gln Arg Thr Val Ala Val Tyr
465                 470                 475                 480

Ser Leu Lys Ile Ala Gly Trp His Gly Pro Lys Ala Pro Tyr Thr Ser
                485                 490                 495

Thr Leu Leu Pro Pro Glu Leu Ser Glu Thr Pro Asn Ala Thr Gln Pro
            500                 505                 510

Glu Leu Ala Pro Glu Asp Pro Glu Asp Ser Ala Leu Leu Glu Asp Pro
        515                 520                 525

Val Gly Thr Val Ala Pro Gln Ile Pro Pro Asn Trp His Ile Pro Ser
        530                 535                 540

Ile Gln Asp Ala Ala Thr Pro Tyr His Pro Pro Ala Thr Pro Asn Asn
545                 550                 555                 560

Met Gly Leu Ile Ala Gly Ala Val Gly Gly Ser Leu Leu Ala Ala Leu
            565                 570                 575

Val Ile Cys Gly Ile Val Tyr Trp Met Arg Arg Arg Thr Gln Lys Ala
        580                 585                 590

Pro Lys Arg Ile Arg Leu Pro His Ile Arg Glu Asp Asp Gln Pro Ser
        595                 600                 605

Ser His Gln Pro Leu Phe Tyr
610                 615
```

<210> SEQ ID NO 8
<211> LENGTH: 619
<212> TYPE: PRT
<213> ORGANISM: Artificial Sequence
<220> FEATURE:
<223> OTHER INFORMATION: gD as in R-VG807

<400> SEQUENCE: 8

```
Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Ser Asp
            20                  25                  30

Ile Gln Met Thr Gln Ser Pro Ser Ser Leu Ser Ala Ser Val Gly Asp
        35                  40                  45

Arg Val Thr Ile Thr Cys Arg Ala Ser Gln Asp Val Asn Thr Ala Val
    50                  55                  60

Ala Trp Tyr Gln Gln Lys Pro Gly Lys Ala Pro Lys Leu Leu Ile Tyr
65                  70                  75                  80

Ser Ala Ser Phe Leu Tyr Ser Gly Val Pro Ser Arg Phe Ser Gly Ser
                85                  90                  95

Arg Ser Gly Thr Asp Phe Thr Leu Thr Ile Ser Ser Leu Gln Pro Glu
            100                 105                 110

Asp Phe Ala Thr Tyr Tyr Cys Gln Gln His Tyr Thr Thr Pro Pro Thr
        115                 120                 125

Phe Gly Gln Gly Thr Lys Val Glu Ile Lys Ser Asp Met Pro Met Ala
130                 135                 140

Asp Pro Asn Arg Phe Arg Gly Lys Asn Leu Val Phe His Ser Glu Val
145                 150                 155                 160

Gln Leu Val Glu Ser Gly Gly Gly Leu Val Gln Pro Gly Gly Ser Leu
                165                 170                 175

Arg Leu Ser Cys Ala Ala Ser Gly Phe Asn Ile Lys Asp Thr Tyr Ile
            180                 185                 190

His Trp Val Arg Gln Ala Pro Gly Lys Gly Leu Glu Trp Val Ala Arg
        195                 200                 205

Ile Tyr Pro Thr Asn Gly Tyr Thr Arg Tyr Ala Asp Ser Val Lys Gly
    210                 215                 220

Arg Phe Thr Ile Ser Ala Asp Thr Ser Lys Asn Thr Ala Tyr Leu Gln
225                 230                 235                 240

Met Asn Ser Leu Arg Ala Glu Asp Thr Ala Val Tyr Tyr Cys Ser Arg
                245                 250                 255

Trp Gly Gly Asp Gly Phe Tyr Ala Met Asp Tyr Trp Gly Gln Gly Thr
            260                 265                 270

Leu Val Thr Val Ser Ser Ser Ala Gly Ser Ala Ser Ser Ala Ser
        275                 280                 285

His Ile Gln Ala Gly Leu Pro Asp Pro Phe Gln Pro Pro Ser Leu Pro
    290                 295                 300

Ile Thr Val Tyr Tyr Ala Val Leu Glu Arg Ala Cys Arg Ser Val Leu
305                 310                 315                 320

Leu Asn Ala Pro Ser Glu Ala Pro Gln Ile Val Arg Gly Ala Ser Glu
                325                 330                 335

Asp Val Arg Lys Gln Pro Tyr Asn Leu Thr Ile Ala Trp Phe Arg Met
            340                 345                 350

Gly Gly Asn Cys Ala Ile Pro Ile Thr Val Met Glu Tyr Thr Glu Cys
        355                 360                 365
```

Ser Tyr Asn Lys Ser Leu Gly Ala Cys Pro Ile Arg Thr Gln Pro Arg
370                 375                 380

Trp Asn Tyr Tyr Asp Ser Phe Ser Ala Val Ser Glu Asp Asn Leu Gly
385                 390                 395                 400

Phe Leu Met His Ala Pro Ala Phe Glu Thr Ala Gly Thr Tyr Leu Arg
            405                 410                 415

Leu Val Lys Ile Asn Asp Trp Thr Glu Ile Thr Gln Phe Ile Leu Glu
            420                 425                 430

His Arg Ala Lys Gly Ser Cys Lys Tyr Ala Leu Pro Leu Arg Ile Pro
            435                 440                 445

Pro Ser Ala Cys Leu Ser Pro Gln Ala Tyr Gln Gln Gly Val Thr Val
450                 455                 460

Asp Ser Ile Gly Met Leu Pro Arg Phe Ile Pro Glu Asn Gln Arg Thr
465                 470                 475                 480

Val Ala Val Tyr Ser Leu Lys Ile Ala Gly Trp His Gly Pro Lys Ala
            485                 490                 495

Pro Tyr Thr Ser Thr Leu Leu Pro Pro Glu Leu Ser Glu Thr Pro Asn
            500                 505                 510

Ala Thr Gln Pro Glu Leu Ala Pro Glu Asp Pro Glu Asp Ser Ala Leu
            515                 520                 525

Leu Glu Asp Pro Val Gly Thr Val Ala Pro Gln Ile Pro Pro Asn Trp
530                 535                 540

His Ile Pro Ser Ile Gln Asp Ala Ala Thr Pro Tyr His Pro Pro Ala
545                 550                 555                 560

Thr Pro Asn Asn Met Gly Leu Ile Ala Gly Ala Val Gly Gly Ser Leu
            565                 570                 575

Leu Ala Ala Leu Val Ile Cys Gly Ile Val Tyr Trp Met Arg Arg Arg
            580                 585                 590

Thr Gln Lys Ala Pro Lys Arg Ile Arg Leu Pro His Ile Arg Glu Asp
            595                 600                 605

Asp Gln Pro Ser Ser His Gln Pro Leu Phe Tyr
        610                 615

<210> SEQ ID NO 9
<211> LENGTH: 361
<212> TYPE: PRT
<213> ORGANISM: Artificial Sequence
<220> FEATURE:
<223> OTHER INFORMATION: gD as in R-VG809

<400> SEQUENCE: 9

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala His Ile
            20                  25                  30

Gln Ala Gly Leu Pro Asp Pro Phe Gln Pro Pro Ser Leu Pro Ile Thr
        35                  40                  45

Val Tyr Tyr Ala Val Leu Glu Arg Ala Cys Arg Ser Val Leu Leu Asn
50                  55                  60

Ala Pro Ser Glu Ala Pro Gln Ile Val Arg Gly Ala Ser Glu Asp Val
65                  70                  75                  80

Arg Lys Gln Pro Tyr Asn Leu Thr Ile Ala Trp Phe Arg Met Gly Gly
            85                  90                  95

Asn Cys Ala Ile Pro Ile Thr Val Met Glu Tyr Thr Glu Cys Ser Tyr
            100                 105                 110

```
Asn Lys Ser Leu Gly Ala Cys Pro Ile Arg Thr Gln Pro Arg Trp Asn
            115                 120                 125

Tyr Tyr Asp Ser Phe Ser Ala Val Ser Glu Asp Asn Leu Gly Phe Leu
        130                 135                 140

Met His Ala Pro Ala Phe Glu Thr Ala Gly Thr Tyr Leu Arg Leu Val
145                 150                 155                 160

Lys Ile Asn Asp Trp Thr Glu Ile Thr Gln Phe Ile Leu Glu His Arg
                165                 170                 175

Ala Lys Gly Ser Cys Lys Tyr Ala Leu Pro Leu Arg Ile Pro Pro Ser
            180                 185                 190

Ala Cys Leu Ser Pro Gln Ala Tyr Gln Gln Gly Val Thr Val Asp Ser
        195                 200                 205

Ile Gly Met Leu Pro Arg Phe Ile Pro Glu Asn Gln Arg Thr Val Ala
    210                 215                 220

Val Tyr Ser Leu Lys Ile Ala Gly Trp His Gly Pro Lys Ala Pro Tyr
225                 230                 235                 240

Thr Ser Thr Leu Leu Pro Pro Glu Leu Ser Glu Thr Pro Asn Ala Thr
                245                 250                 255

Gln Pro Glu Leu Ala Pro Glu Asp Pro Glu Asp Ser Ala Leu Leu Glu
            260                 265                 270

Asp Pro Val Gly Thr Val Ala Pro Gln Ile Pro Pro Asn Trp His Ile
        275                 280                 285

Pro Ser Ile Gln Asp Ala Ala Thr Pro Tyr His Pro Pro Ala Thr Pro
    290                 295                 300

Asn Asn Met Gly Leu Ile Ala Gly Ala Val Gly Gly Ser Leu Leu Ala
305                 310                 315                 320

Ala Leu Val Ile Cys Gly Ile Val Tyr Trp Met Arg Arg Arg Thr Gln
                325                 330                 335

Lys Ala Pro Lys Arg Ile Arg Leu Pro His Ile Arg Glu Asp Asp Gln
            340                 345                 350

Pro Ser Ser His Gln Pro Leu Phe Tyr
        355                 360

<210> SEQ ID NO 10
<211> LENGTH: 74
<212> TYPE: DNA
<213> ORGANISM: Artificial Sequence
<220> FEATURE:
<223> OTHER INFORMATION: primer gH6_galK_f

<400> SEQUENCE: 10
atgcggtcca tgcccaggcc atccaaaaac catgggtctg tctgctcagt cctgttgaca    60
attaatcatc ggca                                                     74

<210> SEQ ID NO 11
<211> LENGTH: 70
<212> TYPE: DNA
<213> ORGANISM: Artificial Sequence
<220> FEATURE:
<223> OTHER INFORMATION: primer gH5_galK_r

<400> SEQUENCE: 11
tcgtgggggt tattatttg gcgttgcgt ggggtcaggt ccacgactgg tcagcactgt    60
cctgctcctt                                                          70
```

```
<210> SEQ ID NO 12
<211> LENGTH: 801
<212> TYPE: DNA
<213> ORGANISM: Artificial Sequence
<220> FEATURE:
<223> OTHER INFORMATION: pSG-ScFvHER2-SG trastuzumab scFv cassette
      bracketed by Ser-Gly linkers

<400> SEQUENCE: 12
catagtagtg gcggtggctc tggatccgat atccagatga cccagtcccc gagctccctg      60
tccgcctctg tgggcgatag ggtcaccatc acctgccgtg ccagtcagga tgtgaatact     120
gctgtagcct ggtatcaaca gaaaccagga aaagctccga agcttctgat ttactcggca     180
tccttcctct actctggagt cccttctcgc ttctctggta gccgttccgg gacggatttc     240
actctgacca tcagcagtct gcagccggaa gacttcgcaa cttattactg tcagcaacat     300
tatactactc ctcccacgtt cggacagggt accaaggtgg agatcaaatc ggatatgccg     360
atggctgatc cgaaccgttt ccgcggtaag aacctggttt tcattctga ggttcagctg      420 gtggagtctg gcggtggcct ggtgcagcca gggggctcac tccgtttgtc ctgtgcagct     480
tctggcttca acattaaaga cacctatata cactgggtgc gtcaggcccc gggtaagggc     540
ctggaatggg ttgcaaggat ttatcctacg aatggttata ctagatatgc cgatagcgtc     600
aagggccgtt tcactataag cgcagacaca tccaaaaaca cagcctacct acaaatgaac     660
agcttaagag ctgaggacac tgccgtctat tattgtagcc gctggggagg ggacggcttc     720
tatgctatgg actactgggg tcaaggaaca ctagtcaccg tctcctcgag tggcggtggc     780
tctggttccg gtggatccgg t                                               801

<210> SEQ ID NO 13
<211> LENGTH: 78
<212> TYPE: DNA
<213> ORGANISM: Artificial Sequence
<220> FEATURE:
<223> OTHER INFORMATION: primer gH23_8SG_scFv4D5_f

<400> SEQUENCE: 13 tcgtggggggt tattattttg ggcgttgcgt ggggtcaggt ccacgactgg catagtagtg     60
gcggtggctc tggatccg                                                   78

<210> SEQ ID NO 14
<211> LENGTH: 25
<212> TYPE: DNA
<213> ORGANISM: Artificial Sequence
<220> FEATURE:
<223> OTHER INFORMATION: primer scFv4D5_358_r

<400> SEQUENCE: 14
ggaaacggtt cggatcagcc atcgg                                           25

<210> SEQ ID NO 15
<211> LENGTH: 74
<212> TYPE: DNA
<213> ORGANISM: Artificial Sequence
<220> FEATURE:
<223> OTHER INFORMATION: primer gH24_12SG_scFv4D5r

<400> SEQUENCE: 15
atgcggtcca tgcccaggcc atccaaaaac catgggtctg tctgctcagt accggatcca     60
ccggaaccag agcc                                                       74
```

<210> SEQ ID NO 16
<211> LENGTH: 26
<212> TYPE: DNA
<213> ORGANISM: Artificial Sequence
<220> FEATURE:
<223> OTHER INFORMATION: primer scFv4D5_315_f

<400> SEQUENCE: 16
ggagatcaaa tcggatatgc cgatgg                                           26

<210> SEQ ID NO 17
<211> LENGTH: 8
<212> TYPE: PRT
<213> ORGANISM: Artificial Sequence
<220> FEATURE:
<223> OTHER INFORMATION: linker

<400> SEQUENCE: 17

His Ser Ser Gly Gly Gly Ser Gly
1               5

<210> SEQ ID NO 18
<211> LENGTH: 12
<212> TYPE: PRT
<213> ORGANISM: Artificial Sequence
<220> FEATURE:
<223> OTHER INFORMATION: linker

<400> SEQUENCE: 18

Ser Ser Gly Gly Gly Ser Gly Ser Gly Gly Ser Gly
1               5                   10

<210> SEQ ID NO 19
<211> LENGTH: 20
<212> TYPE: PRT
<213> ORGANISM: Artificial Sequence
<220> FEATURE:
<223> OTHER INFORMATION: linker

<400> SEQUENCE: 19

Ser Asp Met Pro Met Ala Asp Pro Asn Arg Phe Arg Gly Lys Asn Leu
1               5                   10                  15

Val Phe His Ser
            20

<210> SEQ ID NO 20
<211> LENGTH: 74
<212> TYPE: DNA
<213> ORGANISM: Artificial Sequence
<220> FEATURE:
<223> OTHER INFORMATION: primer UL37/38_galK_f

<400> SEQUENCE: 20
ccgcaggcgt tgcgagtacc ccgcgtcttc gcggggtgtt atacggccac cctgttgaca     60
attaatcatc ggca                                                       74

<210> SEQ ID NO 21
<211> LENGTH: 70
<212> TYPE: DNA
<213> ORGANISM: Artificial Sequence
<220> FEATURE:
<223> OTHER INFORMATION: primer UL37/38_galK_r

<400> SEQUENCE: 21
tccggacaat cccccgggcc tgggtccgcg aacgggatgc cgggacttaa tcagcactgt    60
cctgctcctt                                                            70

<210> SEQ ID NO 22
<211> LENGTH: 72
<212> TYPE: DNA
<213> ORGANISM: Artificial Sequence
<220> FEATURE:
<223> OTHER INFORMATION: primer UL37/38_CMV_mcherry_f

<400> SEQUENCE: 22
ccgcaggcgt tgcgagtacc ccgcgtcttc gcggggtgtt atacggccac cgatgtacgg    60
gccagatata cg                                                         72

<210> SEQ ID NO 23
<211> LENGTH: 70
<212> TYPE: DNA
<213> ORGANISM: Artificial Sequence
<220> FEATURE:
<223> OTHER INFORMATION: primer UL37/38_pA_mcherry_1958_r

<400> SEQUENCE: 23
tccggacaat cccccgggcc tgggtccgcg aacgggatgc cgggacttaa ccatagagcc    60
caccgcatcc                                                            70

<210> SEQ ID NO 24
<211> LENGTH: 74
<212> TYPE: DNA
<213> ORGANISM: Artificial Sequence
<220> FEATURE:
<223> OTHER INFORMATION: primer gH29_galK_f

<400> SEQUENCE: 24
cgcggtggtt tttgggggtc gggggtgttt ggcagccaca gacgcccggt cctgttgaca    60
attaatcatc ggca                                                       74

<210> SEQ ID NO 25
<211> LENGTH: 70
<212> TYPE: DNA
<213> ORGANISM: Artificial Sequence
<220> FEATURE:
<223> OTHER INFORMATION: primer gH5_galK_r

<400> SEQUENCE: 25
tcgtgggggt tattattttg ggcgttgcgt ggggtcaggt ccacgactgg tcagcactgt    60
cctgctcctt                                                            70

<210> SEQ ID NO 26
<211> LENGTH: 74
<212> TYPE: DNA
<213> ORGANISM: Artificial Sequence
<220> FEATURE:
<223> OTHER INFORMATION: primer gH48_12SG_scFv4D5_r

<400> SEQUENCE: 26
ccgcgcggtg gttttgggg gtcgggggtg tttggcagcc acagacgccc accggatcca    60
ccggaaccag agcc                                                       74

```
<210> SEQ ID NO 27
<211> LENGTH: 26
<212> TYPE: DNA
<213> ORGANISM: Artificial Sequence
<220> FEATURE:
<223> OTHER INFORMATION: primer scFv4D5_315_f

<400> SEQUENCE: 27
ggagatcaaa tcggatatgc cgatgg                                          26

<210> SEQ ID NO 28
<211> LENGTH: 27
<212> TYPE: DNA
<213> ORGANISM: Artificial Sequence
<220> FEATURE:
<223> OTHER INFORMATION: primer galK_129_f

<400> SEQUENCE: 28
acaatctctg tttgccaacg catttgg                                         27

<210> SEQ ID NO 29
<211> LENGTH: 27
<212> TYPE: DNA
<213> ORGANISM: Artificial Sequence
<220> FEATURE:
<223> OTHER INFORMATION: primer galK_417_r

<400> SEQUENCE: 29
cattgccgct gatcaccatg tccacgc                                         27

<210> SEQ ID NO 30
<211> LENGTH: 74
<212> TYPE: DNA
<213> ORGANISM: Artificial Sequence
<220> FEATURE:
<223> OTHER INFORMATION: primer gD5_galK_f

<400> SEQUENCE: 30
ttgtcgtcat agtgggcctc catggggtcc gcggcaaata tgccttggcg cctgttgaca     60
attaatcatc ggca                                                       74

<210> SEQ ID NO 31
<211> LENGTH: 70
<212> TYPE: DNA
<213> ORGANISM: Artificial Sequence
<220> FEATURE:
<223> OTHER INFORMATION: primer gD39_galK_r

<400> SEQUENCE: 31
atcgggaggc tgggggggctg aacgggtcc ggtaggcccg cctggatgtg tcagcactgt     60
cctgctcctt                                                            70

<210> SEQ ID NO 32
<211> LENGTH: 100
<212> TYPE: DNA
<213> ORGANISM: Artificial Sequence
<220> FEATURE:
<223> OTHER INFORMATION: oligonucleotide gD_aa5_39_f_r

<400> SEQUENCE: 32
ttgtcgtcat agtgggcctc catggggtcc gcggcaaata tgccttggcg cacatccagg     60
cgggcctacc ggaccccgttc agcccccca gcctcccgat                          100
```

```
<210> SEQ ID NO 33
<211> LENGTH: 74
<212> TYPE: DNA
<213> ORGANISM: Artificial Sequence
<220> FEATURE:
<223> OTHER INFORMATION: primer gD5_galK_f

<400> SEQUENCE: 33
ttgtcgtcat agtgggcctc catggggtcc gcggcaaata tgccttggcg cctgttgaca      60
attaatcatc ggca                                                       74

<210> SEQ ID NO 34
<211> LENGTH: 70
<212> TYPE: DNA
<213> ORGANISM: Artificial Sequence
<220> FEATURE:
<223> OTHER INFORMATION: gD39_galK_r

<400> SEQUENCE: 34
atcgggaggc tgggggctg gaacgggtcc ggtaggcccg cctggatgtg tcagcactgt      60
cctgctcctt                                                            70

<210> SEQ ID NO 35
<211> LENGTH: 73
<212> TYPE: DNA
<213> ORGANISM: Artificial Sequence
<220> FEATURE:
<223> OTHER INFORMATION: primer BAC_LM611_f

<400> SEQUENCE: 35
ttgtcgtcat agtgggcctc catggggtcc gcggcaaata tgccttggcg gccgaggtgc      60
aactgcagca gtc                                                        73

<210> SEQ ID NO 36
<211> LENGTH: 106
<212> TYPE: DNA
<213> ORGANISM: Artificial Sequence
<220> FEATURE:
<223> OTHER INFORMATION: gD39_11SAG_EGFR_r

<400> SEQUENCE: 36
atcgggaggc tgggggctg gaacgggtcc ggtaggcccg cctggatgtg acttgcacta      60
gatgaagcac ttcctgcgga agatttgatc tcgagttctg tccccg                    106

<210> SEQ ID NO 37
<211> LENGTH: 11
<212> TYPE: PRT
<213> ORGANISM: Artificial Sequence
<220> FEATURE:
<223> OTHER INFORMATION: linker

<400> SEQUENCE: 37

Ser Ser Ala Gly Ser Ala Ser Ser Ser Ala Ser
1               5                   10

<210> SEQ ID NO 38
<211> LENGTH: 15
<212> TYPE: PRT
<213> ORGANISM: Artificial Sequence
<220> FEATURE:
<223> OTHER INFORMATION: linker
```

<400> SEQUENCE: 38

Gly Gly Gly Gly Ser Gly Gly Gly Gly Ser Gly Gly Gly Gly Ser
1               5                   10                  15

<210> SEQ ID NO 39
<211> LENGTH: 74
<212> TYPE: DNA
<213> ORGANISM: Artificial Sequence
<220> FEATURE:
<223> OTHER INFORMATION: primer gD5_galK_f

<400> SEQUENCE: 39
ttgtcgtcat agtgggcctc catggggtcc gcggcaaata tgccttggcg cctgttgaca      60
attaatcatc ggca                                                        74

<210> SEQ ID NO 40
<211> LENGTH: 70
<212> TYPE: DNA
<213> ORGANISM: Artificial Sequence
<220> FEATURE:
<223> OTHER INFORMATION: primer gD39_galK_r

<400> SEQUENCE: 40
atcgggaggc tgggggctg gaacgggtcc ggtaggcccg cctggatgtg tcagcactgt      60
cctgctcctt                                                             70

<210> SEQ ID NO 41
<211> LENGTH: 75
<212> TYPE: DNA
<213> ORGANISM: Artificial Sequence
<220> FEATURE:
<223> OTHER INFORMATION: primer gD5_scFvHER2_f

<400> SEQUENCE: 41
ttgtcgtcat agtgggcctc catggggtcc gcggcaaata tgccttggcg tccgatatcc      60
agatgaccca gtccc                                                       75

<210> SEQ ID NO 42
<211> LENGTH: 110
<212> TYPE: DNA
<213> ORGANISM: Artificial Sequence
<220> FEATURE:
<223> OTHER INFORMATION: primer gD39_11SAG_HER2_r

<400> SEQUENCE: 42
atcgggaggc tgggggctg gaacgggtcc ggtaggcccg cctggatgtg acttgcacta      60
gatgaagcac ttcctgcgga agaggagacg gtgactagtg ttccttgacc               110

<210> SEQ ID NO 43
<211> LENGTH: 11
<212> TYPE: PRT
<213> ORGANISM: Artificial Sequence
<220> FEATURE:
<223> OTHER INFORMATION: linker

<400> SEQUENCE: 43

Ser Ser Ala Gly Ser Ala Ser Ser Ser Ala Ser
1               5                   10

<210> SEQ ID NO 44
<211> LENGTH: 20
<212> TYPE: PRT
<213> ORGANISM: Artificial Sequence

```
<220> FEATURE:
<223> OTHER INFORMATION: linker

<400> SEQUENCE: 44

Ser Asp Met Pro Met Ala Asp Pro Asn Arg Phe Arg Gly Lys Asn Leu
1               5                   10                  15

Val Phe His Ser
            20
```